United States Patent
Greenwood et al.

(10) Patent No.: US 10,336,752 B2
(45) Date of Patent: Jul. 2, 2019

(54) TYK2 INHIBITORS, USES, AND METHODS FOR PRODUCTION THEREOF

(71) Applicant: Nimbus Lakshmi, Inc., Cambridge, MA (US)

(72) Inventors: Jeremy Robert Greenwood, Brooklyn, NY (US); Jon P. Lawson, Cambridge, MA (US); Craig E. Masse, Cambridge, MA (US); Jean-Baptiste Arlin, Almere (NL); David Pearson, Lauder (GB); Jonathan James Loughrey, Edinburgh (GB)

(73) Assignee: Nimbus Lakshmi, Inc., Cambridge, MA (US)

( * ) Notice: Subject to any disclaimer, the term of this patent is extended or adjusted under 35 U.S.C. 154(b) by 0 days.

(21) Appl. No.: 15/914,074

(22) Filed: Mar. 7, 2018

(65) Prior Publication Data

US 2018/0258086 A1    Sep. 13, 2018

Related U.S. Application Data

(60) Provisional application No. 62/468,688, filed on Mar. 8, 2017.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01); *C07B 2200/13* (2013.01)

(58) Field of Classification Search
CPC .. C07B 2200/13; C07D 471/04; C07D 519/00
See application file for complete search history.

(56) References Cited

U.S. PATENT DOCUMENTS

| | | | |
|---|---|---|---|
| 6,552,065 B2 | 4/2003 | Remiszewski et al. |
| 7,390,799 B2 | 6/2008 | Bruncko et al. |
| 8,138,347 B2 | 3/2012 | Adams et al. |
| 9,630,970 B2 | 4/2017 | Masse et al. |
| 10,023,571 B2 | 7/2018 | Masse et al. |
| 2013/0231340 A1 | 9/2013 | Reader |
| 2015/0166513 A1 | 6/2015 | Harrison et al. |
| 2016/0251376 A1 | 9/2016 | Dahlgren et al. |
| 2018/0134700 A1 | 5/2018 | Greenwood et al. |

(Continued)

FOREIGN PATENT DOCUMENTS

| | | |
|---|---|---|
| WO | 2001042246 | 6/2001 |
| WO | 2002088112 | 11/2002 |
| WO | 2003063794 | 8/2003 |

(Continued)

OTHER PUBLICATIONS

Bacon et al., "Interleukin 12 (IL-12) induces tyrosine phosphorylation of Jak2 and Tyk2: differential use of Janus family kinases by IL-2 and IL-12," Journal of Experimental Medicine, vol. 181, No. 1, Jan. 1995 (pp. 399-404).

(Continued)

*Primary Examiner* — Valerie Rodriguez-Garcia
(74) *Attorney, Agent, or Firm* — Andrea L.C. Reid; Dechert LLP

(57) ABSTRACT

The present invention provides compounds useful as inhibitors of Tyrosine Kinase 2 (Tyk2), solid forms and compositions thereof, methods of producing the same, and methods of using the same in the treatment of Tyk2-mediated diseases.

16 Claims, 7 Drawing Sheets

(56) References Cited

U.S. PATENT DOCUMENTS

2018/0155349 A1    6/2018   Greenwood et al.

FOREIGN PATENT DOCUMENTS

| | | |
|---|---|---|
| WO | 2004019973 | 3/2004 |
| WO | 2004089925 | 10/2004 |
| WO | 2004106328 | 12/2004 |
| WO | 2005007623 | 1/2005 |
| WO | 2005113554 | 12/2005 |
| WO | 2006078846 | 7/2006 |
| WO | 2006122806 | 11/2006 |
| WO | 2007016176 | 2/2007 |
| WO | 2007044729 | 4/2007 |
| WO | 2007053452 | 5/2007 |
| WO | 2007070514 | 6/2007 |
| WO | 2007084786 | 7/2007 |
| WO | 2007129161 | 11/2007 |
| WO | 2008039218 | 4/2008 |
| WO | 2008109943 | 9/2008 |
| WO | 2008118802 | 10/2008 |
| WO | 2009114512 | 9/2009 |
| WO | 2011090760 | 7/2011 |
| WO | 2014074660 A1 | 5/2014 |
| WO | 2014074661 A1 | 5/2014 |
| WO | 2015089143 A1 | 6/2015 |
| WO | 2015131080 A1 | 9/2015 |

OTHER PUBLICATIONS

Ban et al., "Replication analysis identifies TYK2 as a multiple sclerosis susceptibility factor," European Journal of Human Genetics, vol. 17, No. 10, Apr. 2009 (pp. 1309-1313).

Berge et al., "Pharmaceutical Salts," Journal of Pharmaceutical Sciences, vol. 66, No. 1, Jan. 1977 (pp. 1-19).

Cho et al., "Genomics and the multifactorial nature of human auto-immune disease," New England Journal of Medicine, vol. 365, No. 17, Oct. 2011 (pp. 1612-1623).

Cortes et al., "Identification of multiple risk variants for ankylosing spondylitis through high-density genotyping of immune-related loci," Nature Genetics, vol. 45, No. 7, Jul. 2013 (pp. 730-738).

Duerr et al., "A Genome-Wide Association Study Identifies IL23R as an Inflammatory Bowel Disease Gene," Science, vol. 314, No. 5804, Dec. 2006 (pp. 1461-1463).

Finbloom et al., "IL-10 induces the tyrosine phosphorylation of Tyk2 and Jak1 and the differential assembly of Stat1 and Stat3 complexes in human T cells and monocytes," Journal of Immunology, vol. 155, No. 3, Aug. 1995 (pp. 1079-1090).

Fontan et al. "Discovering What Makes STAT Signaling TYK in T-ALL," Cancer Discovery, vol. 3, No. 5, May 2013 (pp. 494-496).

Graham et al., "Association of NCF2, IKZF1, IRF8, IFIH1, and TYK2 with Systemic Lupus Erythematosus," PLoS Genetics, vol. 7, No. 10, Oct. 2011 (9 pages).

Harel et al., "Pharmacologic inhibition of JAK-STAT signaling promotes hair growth," Science Advances, vol. 1, No. 9, Oct. 2015 (12 pages).

Ishizaki et al., "Tyk2 deficiency protects joints against destruction in anti-type II collagen antibody-induced arthritis in mice," International Immunology, vol. 23, No. 9, Sep. 2011 (pp. 575-582).

Ishizaki et al., "Tyk2 is a therapeutic target for psoriasis-like skin inflammation," International Immunology, vol. 26, No. 5, May 2013 (pp. 257-267).

Oyamada et al., "Tyrosine Kinase 2 Plays Critical Roles in the Pathogenic CD4 T Cell Responses for the Development of Experimental Autoimmune Encephalomyelitis," Journal of Immunology, vol. 183, No. 11, Dec. 2009 (7539-7546).

Parham et al., "A receptor for the heterodimeric cytokine IL-23 is composed of IL-12Rβ1 and a novel cytokine receptor subunit, IL-23R," Journal of Immunology, vol. 168, No. 11, Jun. 2002 (pp. 5699-5708).

Ramirez et al., "Defining causative factors contributing in the activation of hedgehog signaling in diffuse large B-cell lymphoma," Leukemia Research, vol. 36, No. 10, Jul. 2012 (pp. 1267-1273).

Remmers et al., "Genome-wide association study identifies variants in the MHC class I, IL10, and IL23R-IL12RB2 regions associated with Behçet's disease," Nature Genetics, vol. 42, No. 8, Aug. 2010 (pp. 698-702).

Sanda et al. "TYK2-STAT1-BCL2 Pathway Dependence in T-Cell Acute Lymphoblastic Leukemia," Cancer Discovery, vol. 3, No. 5, May 2013 (pp. 564-577).

Sigurdsson et al., "Polymorphisms in the Tyrosine Kinase 2 and Interferon Regulatory Factor 5 Genes Are Associated with Systemic Lupus Erythematosus," American Journal of Human Genetics, vol. 76, No. 3, Mar. 2005 (pp. 528-537).

Simma et al. "Identification of an Indispensable Role for Tyrosine Kinase 2 in CTL-Mediated Tumor Surveillance," Cancer Research, vol. 69, No. 1, Jan. 2009 (pp. 203-211).

Stahl et al., "Association and activation of Jak-Tyk kinases by CNTF-LIF-OSM-IL-6β receptor components," Science, vol. 263, No. 5143, Jan. 1994 (pp. 92-95).

Strange et al., "A genome-wide association study identifies new psoriasis susceptibility loci and an interaction between HLA-C and ERAP1," Nature Genetic, vol. 42, No. 11, Nov. 2010 (pp. 985-990).

Velasquez et al., "A protein kinase in the interferon α/β signaling pathway," Cell, vol. 70, No. 2, Jul. 1992 (pp. 313-322).

Wan et al. "Tyk/STAT3 Signaling Mediates β-Amyloid-Induced Neuronal Cell Death: Implications in Alzheimer's Disease," Journal of Neuroscience, vol. 30, No. 20, May 2010 (pp. 6873-6881).

Welham et al., "Interleukin-13 signal transduction in lymphohemopoietic cells: similarities and differences in signal transduction with interleukin-4 and insulin," Journal of Biological Chemistry, vol. 270, No. 20, Jun. 1995 (pp. 12286-12296).

Xing et al., "Alopecia areata is driven by cytotoxic T lymphocytes and is reversed by JAK inhibition," Nature Medicine, vol. 20, No. 9, Sep. 2014 (pp. 1043-1049).

Zhang et al., "Docking protein Gab2 regulates mucin expression and goblet cell hyperplasia through TYK2/STAT6 pathway," FASEB Journal, vol. 26, No. 11, Nov. 2012 (pp. 4603-4613).

International Search Report and Written Opinion issued by the United States Patent and Trademark Office as International Searching Authority for International Application No. PCT/US2018/021265, dated Jul. 10, 2018 (11 pages).

PubChem, XDTKWAGKBLDFOE-UHFFFAOYSA-N, CID 118348179, Feb. 23, 2016 (12 page).

TYK2 INHIBITORS, USES, AND METHODS FOR PRODUCTION THEREOF

TECHNICAL FIELD OF THE INVENTION

The present invention relates to compounds and methods useful for inhibiting non-receptor tyrosine-protein kinase 2 ("TYK2"), also known as Tyrosine kinase 2. The invention also provides solid forms of those compounds, pharmaceutically acceptable compositions comprising said compounds, processes for producing said compounds, and methods of using said compounds and compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is the protein kinase family.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxins, and $H_2O_2$), cytokines (e.g., interleukin-1 (IL-1), interleukin-8 (IL-8), and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by kinase-mediated events. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

DETAILED DESCRIPTION OF CERTAIN EMBODIMENTS

Figure 1:
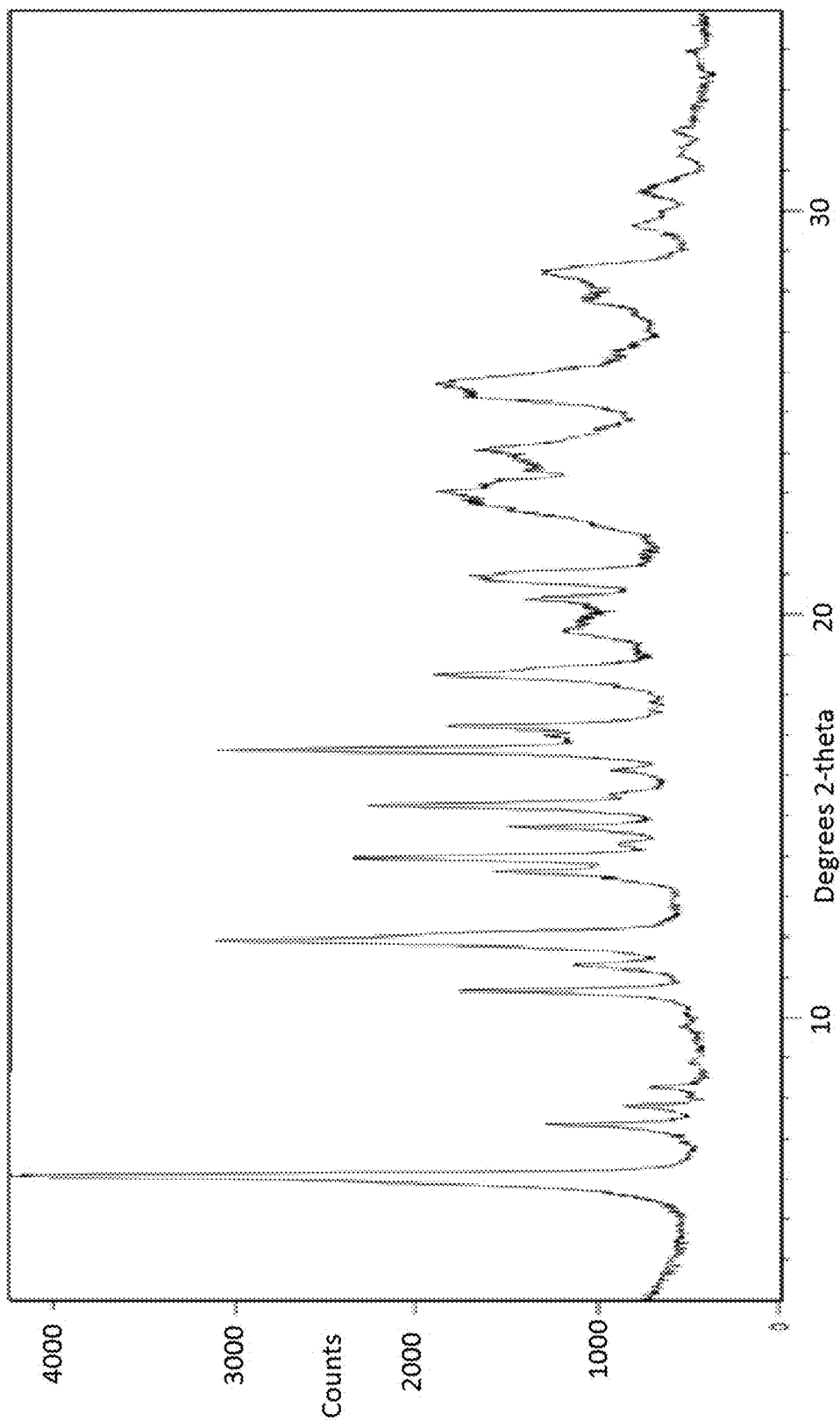
FIG. 1 depicts an X-Ray powder diffraction (XRPD) pattern of Form I' of the free base of Compound 1.

General Description of Certain Aspects of the Invention:

It has now surprisingly been found that compounds of the following formula I, and pharmaceutically acceptable salts thereof, are potent and selective inhibitors of Tyk2 having favorable drug-like properties

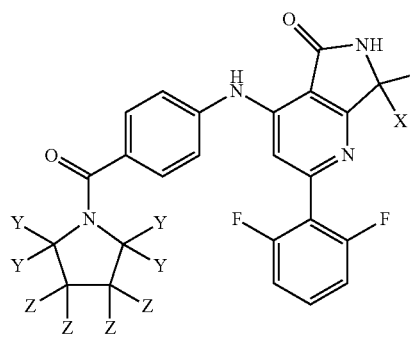

wherein each of X, Y, and Z is independently hydrogen or deuterium.

Compounds of formula I are active in a variety of assays and therapeutic models, including those demonstrating inhibition of Tyk2, treatment of proliferative disorders, and of inflammatory disease.

Additionally, the present invention provides solid forms of compounds of formula I, and pharmaceutically acceptable salts thereof, that impart desirable characteristics such as improved aqueous solubility, stability, and ease of formulation.

Also disclosed are novel synthetic methods for producing compounds of formula I, as well as novel intermediates in the synthesis of such compounds. Such methods and intermediates are amenable to large scale production, owing to high yields, favorable physicochemical properties, and reduced use of toxic reagents or solvents compared to the state of the art.

Compounds

As described generally above, the present invention provides compounds of formula I:

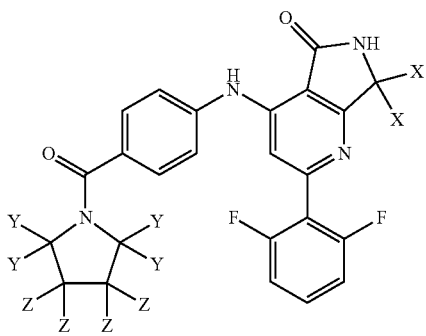

wherein each of X, Y, and Z is independently hydrogen or deuterium.

In some embodiments, X is hydrogen. In some embodiments, X is deuterium.

In some embodiments, Y is hydrogen. In some embodiments, Y is deuterium.

In some embodiments, Z is hydrogen. In some embodiments, Z is deuterium.

In some embodiments, each of X, Y, and Z is hydrogen, thereby providing Compound

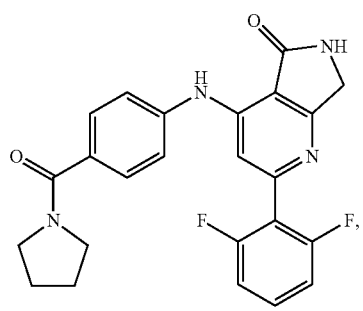 [SMILES: O=C1NCc2nc(-c3c(F)cccc3F)cc(Nc3ccc(C(=O)N4CCCC4)cc3)c21]

depicted here as its free base. However, for the avoidance of doubt, unless otherwise stated, the term "Compound 1" is intended to cover the compound depicted above as either its free base or a pharmaceutically acceptable salt thereof.

In some embodiments, the present invention provides the mesylate salt of Compound 1, also denoted herein as Compound 1M:

Compound 1M

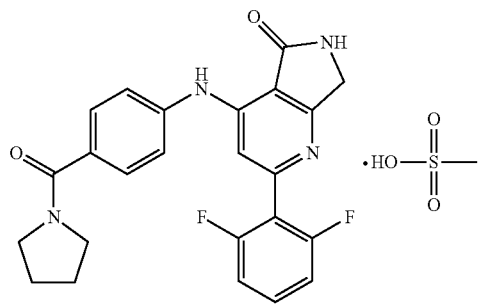

In some embodiments, the present invention provides a compound of formula I bearing one or more deuterium atoms in place of hydrogen (i.e. where one or more of X, Y, or Z is deuterium), or a pharmaceutically acceptable salt thereof. In some embodiments, such compounds include the following, or a pharmaceutically acceptable salt thereof:

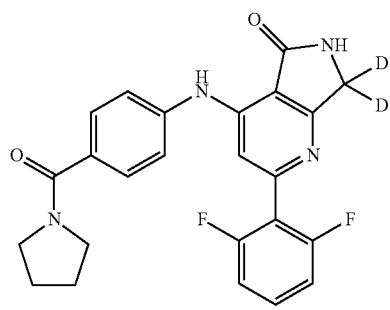

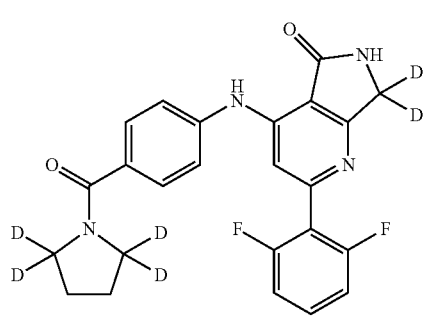

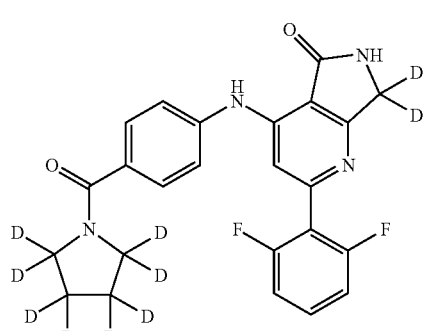

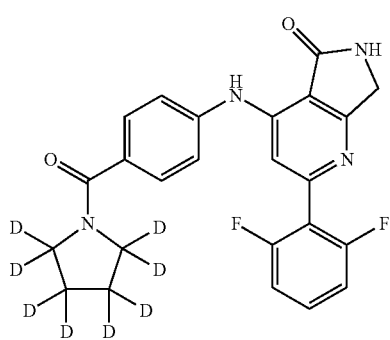

-continued

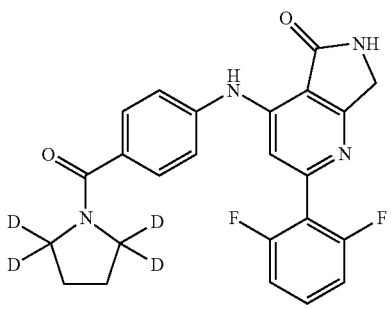

6

In some embodiments, the present invention provides the mesylate salt of a compound of Formula I. In some embodiments, the present invention provides the mesylate salt of one of compounds 2, 3, 4, 5, or 6 in the table above.

Solid Forms of Compound 1

In some embodiments, the present invention provides a solid form of Compound 1. In some embodiments, the present invention provides a solid form of Compound 1 that is substantially free of impurities. As used herein, the term "substantially free of impurities" means that the compound contains no significant amount of extraneous matter. Such extraneous matter may include residual solvents, or any other impurities that may result from the preparation of, and/or isolation of, Compound 1. In certain embodiments, at least about 95% by weight of Compound 1 is present. In still other embodiments of the invention, at least about 99% by weight of Compound 1 is present.

According to one embodiment, Compound 1 is present in an amount of at least about 97.0, 97.5, 98.0, 98.5, 99.0, 99.5, or 99.8 weight percent where the percentages are based on the total weight of the composition. According to another embodiment, Compound 1 contains no more that about 3.0 area percent HPLC of total organic impurities and, in certain embodiments, no more that about 1.5 area percent HPLC total organic impurities relative to the total area of the HPLC chromatogram. In other embodiments, Compound 1 contains no more than about 1.0% area percent HPLC of any single impurity, and, in certain embodiments, no more than about 0.5 area percent HPLC of any single impurity, relative to the total area of the HPLC chromatogram.

In some embodiments, Compound 1 is present as a free base. In some embodiments, Compound 1 is present as a pharmaceutically acceptable salt.

In some embodiments, the present invention provides a solid form of the free base of Compound 1. In some embodiments, the present invention provides a solid form of Compound 1 as a pharmaceutically acceptable salt. In some embodiments, the present invention provides a solid form of Compound 1M.

The structure depicted for Compound 1 is also meant to include all tautomeric forms of Compound 1. Additionally structures depicted here are also meant to include compounds that differ only in the presence of one or more isotopically enriched atoms, in addition to any isotopically enriched atoms that are explicitly defined. For example, compounds having the present structure except for the replacement of hydrogen by deuterium or tritium, or the replacement of a carbon by a $^{13}$C- or $^{14}$C-enriched carbon are within the scope of this invention.

It has been found that Compound 1 can exist in a variety of solid forms. Such forms include polymorphs, solvates, hydrates, and amorphous. All such forms are contemplated by the present invention. In certain embodiments, the present invention provides Compound 1 as a mixture of one or more solid forms selected from polymorphs, solvates, hydrates, and amorphous Compound 1.

In some embodiments, the solid form of Compound 1 is an amorphous solid. In certain embodiments, the present invention provides Compound 1 as an amorphous solid substantially free of crystalline Compound 1. As used herein, the term "substantially free of crystalline Compound 1" means that the compound contains no significant amount of crystalline Compound 1. In certain embodiments, at least about 95% by weight of amorphous Compound 1 is present. In still other embodiments, of the invention, at least about 99% by weight of amorphous Compound 1 is present. In some embodiments, the present invention provides amorphous Compound 1 free base. In some embodiments, the present invention provides amorphous Compound 1 as its pharmaceutically acceptable salt. In some embodiments, the present invention provides amorphous Compound 1M.

As used herein, the term "polymorph" refers to any of the different crystal structures in which a compound can crystallize. As used herein, the term "solvate" refers to a crystal form with either a stoichiometric or non-stoichiometric amount of solvent incorporated into the crystal structure. Similarly, the term "hydrate" refers specifically to a crystal form with either a stoichiometric or non-stoichiometric amount of water incorporated into the crystal structure.

In certain embodiments, the solid form of Compound 1 is a crystalline solid. In some embodiments, Compound 1 is a crystalline solid substantially free of amorphous Compound 1. As used herein, the term "substantially free of amorphous Compound 1" means that the compound contains no significant amount of amorphous Compound 1. In certain embodiments, at least about 95% by weight of crystalline Compound 1 is present. In still other embodiments, of the invention, at least about 99% by weight of crystalline Compound 1 is present.

In some embodiments, the solid form of Compound 1 is a neat crystal form, and thus does not have any water or other solvent incorporated into its crystal structure. It has now been found that Compound 1 can exist in at least one distinct neat (i.e. anhydrous, non-solvate) crystal form. Such neat crystal forms of Compound 1 include Form I of Compound 1 mesylate, of which is described in detail herein.

In some embodiments, the present invention provides a solvated crystalline form of Compound 1. Such solvated crystalline forms of Compound 1 include Form II, Form III, Form IV, and Form V of Compound 1 mesylate, and Form I' of Compound 1 free base.

In some embodiments, the present invention provides a crystalline form of Compound 1 selected from any of those referred to as Form I, Form II, Form III, Form IV, or Form V. Methods for preparing each of Forms I through V and I' of Compound 1 are described herein.

In some embodiments, the present invention provides a polymorphic form of Compound 1 free base referred to as Form I'.

In some embodiments, the present invention provides Form I' of Compound 1, having a powder X-ray diffraction pattern substantially similar to that depicted in FIG. 1.

As used herein, the term "about", when used in reference to a degree 2θ value refers to the stated value±0.1 degree 2θ, obtained under the sample preparation and data collection conditions described in the exemplification. One of skill in the art will appreciate that changes in the particular XRPD acquisition parameters will affect the XRPD pattern and specific values of degrees 2θ obtained.

In some embodiments, Form I' of Compound 1 free base is characterized in that it has one or more peaks in its powder X-ray diffraction pattern selected from those in Table 1 below.

TABLE 1

Compound 1 Form I' XRPD Peaks

| Position (°2θ) | Height (cts) | Relative Intensity (%) |
|---|---|---|
| 6.0700 | 3707.10 | 100.00 |
| 7.3496 | 836.02 | 22.55 |
| 7.8002 | 407.26 | 10.99 |
| 8.2782 | 265.83 | 7.17 |
| 10.6599 | 1241.31 | 33.48 |
| 11.3113 | 599.19 | 16.16 |
| 11.9037 | 2584.87 | 69.73 |
| 12.0950 | 1324.71 | 35.73 |
| 13.6129 | 990.01 | 26.71 |
| 13.9542 | 1758.35 | 47.43 |
| 14.2840 | 291.51 | 7.86 |
| 14.7169 | 877.59 | 23.67 |
| 15.2495 | 1647.47 | 44.44 |
| 16.1252 | 243.38 | 6.57 |
| 16.6247 | 2437.44 | 65.75 |
| 17.2152 | 1134.51 | 30.60 |
| 18.5017 | 1226.40 | 33.08 |
| 19.5802 | 480.66 | 12.97 |
| 20.3658 | 686.09 | 18.51 |
| 20.8783 | 910.68 | 24.57 |
| 21.0155 | 789.21 | 21.29 |
| 23.0207 | 1113.59 | 30.04 |
| 23.2783 | 802.57 | 21.65 |
| 24.0781 | 874.50 | 23.59 |
| 25.4085 | 960.57 | 25.91 |
| 25.7185 | 1165.97 | 31.45 |
| 27.7872 | 434.24 | 11.71 |
| 28.4799 | 712.66 | 19.22 |
| 29.6081 | 290.82 | 7.85 |
| 30.4683 | 272.67 | 7.36 |

In some embodiments, Form I' of Compound 1 free base is characterized in that it has two or more peaks in its powder X-ray diffraction pattern selected from those in Table 1. In some embodiments, Form I' of Compound 1 is characterized in that it has three or more peaks in its powder X-ray diffraction pattern selected from those in Table 1. In some embodiments, Form I' of Compound 1 is characterized in that it has four or more peaks in its powder X-ray diffraction pattern selected from those in Table 1. In some embodiments, Form I' of Compound 1 is characterized in that it has five or more peaks in its powder X-ray diffraction pattern selected from those in Table 1. In some embodiments, Form I' of Compound 1 is characterized in that it has ten of the peaks in Table 1 in its X-ray diffraction pattern. In some embodiments, Form I' of Compound 1 is characterized in that it has fifteen of the peaks in Table 1 in its X-ray diffraction pattern. In some embodiments, Form I' of Compound 1 is characterized in that it has twenty of the peaks in Table 1 in its X-ray diffraction pattern. In some embodiments, Form I' of Compound 1 is characterized in that it has all of the peaks in Table 1 in its X-ray diffraction pattern.

In some embodiments, Form I of Compound 1 is characterized in that it has one or more peaks in its powder X-ray diffraction pattern selected from those at about 6.07, about 11.90, about 16.62, and about 13.95 degrees 2θ. In some embodiments, Form I of Compound 1 is characterized in that it has two or more peaks in its powder X-ray diffraction pattern selected from those at about 6.07, about 11.90, about 16.62, and about 13.95 degrees 2θ. In some embodiments, Form I of Compound 1 is characterized in that it has three or more peaks in its powder X-ray diffraction pattern selected from those at about 6.07, about 11.90, about 16.62, and about 13.95 degrees 2θ. In some embodiments, Form I of Compound 1 is characterized in that it has all four peaks in its powder X-ray diffraction pattern selected from those at about 6.07, about 11.90, about 16.62, and about 13.95 degrees 2θ.

In some embodiments, the present invention provides a neat crystalline form of Compound 1 mesylate referred to as Form I. In some embodiments, the present invention provides Form I of Compound 1, having a powder X-ray diffraction pattern substantially similar to that depicted in FIG. 2. In some embodiments, Form I of Compound 1 is characterized in that it has one or more peaks in its powder X-ray diffraction pattern selected from those in Table 2 below.

TABLE 2

Compound 1 Form I XRPD Peaks

| Position (°2θ) | Height (cts) | Relative Intensity (%) |
|---|---|---|
| 6.4222 | 1147.42 | 21.11 |
| 9.1780 | 3154.55 | 58.05 |
| 11.1364 | 942.06 | 17.34 |
| 12.8488 | 509.43 | 9.37 |
| 13.2993 | 550.44 | 10.13 |
| 13.7913 | 645.33 | 11.87 |
| 14.3702 | 2858.25 | 52.60 |
| 14.9145 | 974.99 | 17.94 |
| 15.9065 | 1315.52 | 24.21 |
| 16.8833 | 2940.50 | 54.11 |
| 17.4864 | 359.10 | 6.61 |
| 18.3945 | 689.97 | 12.70 |
| 19.4147 | 926.98 | 17.06 |
| 19.8920 | 5434.42 | 100.00 |
| 20.2035 | 2099.61 | 38.64 |
| 21.5878 | 728.59 | 13.41 |
| 22.0900 | 2636.56 | 48.52 |
| 22.3198 | 1378.87 | 25.37 |
| 22.9101 | 1703.48 | 31.35 |
| 24.1420 | 1656.01 | 30.47 |
| 24.3748 | 1723.15 | 31.71 |
| 24.8519 | 626.03 | 11.52 |
| 25.5296 | 695.16 | 12.79 |
| 25.8669 | 426.82 | 7.85 |
| 26.4749 | 531.54 | 9.78 |
| 28.4433 | 624.17 | 11.49 |
| 28.9463 | 417.47 | 7.68 |
| 33.4565 | 287.82 | 5.30 |

In some embodiments, Form I of Compound 1 is characterized in that it has two or more peaks in its powder X-ray diffraction pattern selected from those in Table 2. In some embodiments, Form I of Compound 1 is characterized in that it has three or more peaks in its powder X-ray diffraction pattern selected from those in Table 2. In some embodiments, Form I of Compound 1 is characterized in that it has four or more peaks in its powder X-ray diffraction pattern selected from those in Table 2. In some embodiments, Form I of Compound 1 is characterized in that it has five or more peaks in its powder X-ray diffraction pattern selected from those in Table 2. In some embodiments, Form I of Compound 1 is characterized in that it has all of the peaks in Table 2 in its X-ray diffraction pattern.

In some embodiments, Form I of Compound 1 is characterized in that it has one or more peaks in its powder X-ray diffraction pattern selected from those at about 19.89, about 9.17, about 16.88, about 14.37, and about 22.09 degrees 2θ.

In some embodiments, Form I of Compound 1 is characterized in that it has two or more peaks in its powder X-ray diffraction pattern selected from those at about 19.89, about 9.17, about 16.88, about 14.37, and about 22.09 degrees 2θ. In some embodiments, Form I of Compound 1 is characterized in that it has three or more peaks in its powder X-ray diffraction pattern selected from those at about 19.89, about 9.17, about 16.88, about 14.37, and about 22.09 degrees 2θ. In some embodiments, Form I of Compound 1 is characterized in that it has four or more peaks in its powder X-ray diffraction pattern selected from those at about 19.89, about 9.17, about 16.88, about 14.37, and about 22.09 degrees 2θ. In some embodiments, Form I of Compound 1 is characterized in that it has all five peaks in its powder X-ray diffraction pattern selected from those at about 19.89, about 9.17, about 16.88, about 14.37, and about 22.09 degrees 2θ.

In some embodiments, the present invention provides a solvated crystalline form of Compound 1 mesylate referred to as Form II. In some embodiments, the present invention provides Form II of Compound 1, having a powder X-ray diffraction pattern substantially similar to that depicted in FIG. 3. In some embodiments, Form II of Compound 1 is characterized in that it has one or more peaks in its powder X-ray diffraction pattern selected from those in Table 3 below.

TABLE 3

Compound 1 Form II XRPD Peaks

| Position (°2θ) | Height (cts) | Relative Intensity (%) |
|---|---|---|
| 7.9701 | 468.93 | 9.76 |
| 8.5228 | 1009.03 | 21.00 |
| 8.8961 | 2628.33 | 54.70 |
| 11.1290 | 1097.72 | 22.84 |
| 12.8376 | 1017.53 | 21.18 |
| 13.5921 | 493.97 | 10.28 |
| 13.9687 | 389.59 | 8.11 |
| 14.3776 | 432.91 | 9.01 |
| 14.5002 | 381.24 | 7.93 |
| 15.5065 | 239.88 | 4.99 |
| 15.9553 | 884.48 | 18.41 |
| 16.3484 | 2878.72 | 59.91 |
| 16.8545 | 489.38 | 10.18 |
| 17.0635 | 2694.94 | 56.08 |
| 17.5257 | 2143.00 | 44.60 |
| 17.8231 | 481.65 | 10.02 |
| 18.2699 | 1426.17 | 29.68 |
| 18.6763 | 2651.44 | 55.18 |
| 20.0515 | 696.36 | 14.49 |
| 20.2098 | 2505.87 | 52.15 |
| 20.6367 | 1224.33 | 25.48 |
| 21.0566 | 403.56 | 8.40 |
| 21.2443 | 1588.61 | 33.06 |
| 21.6209 | 482.85 | 10.05 |
| 21.9825 | 357.82 | 7.45 |
| 22.2727 | 4805.20 | 100.00 |
| 23.4728 | 1259.25 | 26.21 |
| 23.8021 | 595.12 | 12.38 |
| 24.0065 | 446.43 | 9.29 |
| 25.1612 | 429.55 | 8.94 |
| 25.3060 | 372.12 | 7.74 |
| 25.8238 | 1488.96 | 30.99 |
| 26.0253 | 3229.27 | 67.20 |
| 26.4504 | 3972.97 | 82.68 |
| 26.7143 | 1826.14 | 38.00 |
| 27.3448 | 392.77 | 8.17 |
| 27.5209 | 998.53 | 20.78 |
| 27.8190 | 357.86 | 7.45 |
| 28.1462 | 1975.32 | 41.11 |
| 28.5573 | 694.14 | 14.45 |
| 29.1064 | 441.49 | 9.19 |
| 29.4033 | 598.69 | 12.46 |

TABLE 3-continued

Compound 1 Form II XRPD Peaks

| Position (°2θ) | Height (cts) | Relative Intensity (%) |
|---|---|---|
| 29.5376 | 653.19 | 13.59 |
| 30.1886 | 278.35 | 5.79 |
| 31.8732 | 848.14 | 17.65 |
| 32.5997 | 670.08 | 13.94 |
| 33.0026 | 338.47 | 7.04 |
| 33.6470 | 268.16 | 5.58 |

In some embodiments, Form II of Compound 1 is characterized in that it has two or more peaks in its powder X-ray diffraction pattern selected from those in Table 3. In some embodiments, Form II of Compound 1 is characterized in that it has three or more peaks in its powder X-ray diffraction pattern selected from those in Table 3. In some embodiments, Form II of Compound 1 is characterized in that it has four or more peaks in its powder X-ray diffraction pattern selected from those in Table 3. In some embodiments, Form II of Compound 1 is characterized in that it has five or more peaks in its powder X-ray diffraction pattern selected from those in Table 3. In some embodiments, Form II of Compound 1 is characterized in that it has all of the peaks in Table 3 in its X-ray diffraction pattern.

In some embodiments, Form II of Compound 1 is characterized in that it has one or more peaks in its powder X-ray diffraction pattern selected from those at about 22.27, about 26.45, about 26.02, about 16.34, and about 17.06 degrees 2θ. In some embodiments, Form II of Compound 1 is characterized in that it has two or more peaks in its powder X-ray diffraction pattern selected from those at about 22.27, about 26.45, about 26.02, about 16.34, and about 17.06 degrees 2θ. In some embodiments, Form II of Compound 1 is characterized in that it has three or more peaks in its powder X-ray diffraction pattern selected from those at about 22.27, about 26.45, about 26.02, about 16.34, and about 17.06 degrees 2θ. In some embodiments, Form II of Compound 1 is characterized in that it has four or more peaks in its powder X-ray diffraction pattern selected from those at about 22.27, about 26.45, about 26.02, about 16.34, and about 17.06 degrees 2θ. In some embodiments, Form II of Compound 1 is characterized in that it has all five peaks in its powder X-ray diffraction pattern selected from those at about 22.27, about 26.45, about 26.02, about 16.34, and about 17.06 degrees 2θ.

In some embodiments, the present invention provides a solvated crystalline form of Compound 1 mesylate referred to as Form III. In some embodiments, the present invention provides Form III of Compound 1, having a powder X-ray diffraction pattern substantially similar to that depicted in FIG. 4. In some embodiments, Form III of Compound 1 is characterized in that it has one or more peaks in its powder X-ray diffraction pattern selected from those listed in Table 4 below.

TABLE 4

Compound 1 Form III XRPD Peaks

| Position (°2θ) | Height (cts) | Relative Intensity (%) |
|---|---|---|
| 7.6100 | 318.58 | 34.04 |
| 9.0773 | 96.96 | 10.36 |
| 9.8524 | 353.97 | 37.82 |
| 11.1997 | 78.66 | 8.41 |
| 11.8535 | 255.91 | 27.35 |

TABLE 4-continued

Compound 1 Form III XRPD Peaks

| Position (°2θ) | Height (cts) | Relative Intensity (%) |
|---|---|---|
| 13.1453 | 165.85 | 17.72 |
| 14.2078 | 273.03 | 29.18 |
| 15.6943 | 148.26 | 15.84 |
| 16.9586 | 550.52 | 58.83 |
| 17.2500 | 324.76 | 34.70 |
| 18.1827 | 935.85 | 100.00 |
| 18.5648 | 603.68 | 64.51 |
| 19.7502 | 116.00 | 12.40 |
| 20.1432 | 91.76 | 9.81 |
| 21.9569 | 470.43 | 50.27 |
| 24.3804 | 135.50 | 14.48 |
| 25.4532 | 333.87 | 35.68 |
| 26.4804 | 285.80 | 30.54 |

In some embodiments, Form III of Compound 1 is characterized in that it has two or more peaks in its powder X-ray diffraction pattern selected from those in Table 4. In some embodiments, Form IV of Compound 1 is characterized in that it has three or more peaks in its powder X-ray diffraction pattern selected from those in Table 4. In some embodiments, Form IV of Compound 1 is characterized in that it has four or more peaks in its powder X-ray diffraction pattern selected from those in Table 4. In some embodiments, Form IV of Compound 1 is characterized in that it has five or more peaks in its powder X-ray diffraction pattern selected from those in Table 4. In some embodiments, Form IV of Compound 1 is characterized in that it has all of the peaks in Table 4 in its X-ray diffraction pattern.

In some embodiments, Form IV of Compound 1 is characterized in that it has one or more peaks in its powder X-ray diffraction pattern selected from those at about 18.18, about 18.56, about 16.95, about 21.95, and about 9.85 degrees 2θ. In some embodiments, Form IV of Compound 1 is characterized in that it has two or more peaks in its powder X-ray diffraction pattern selected from those at about 18.18, about 18.56, about 16.95, about 21.95, and about 9.85 degrees 2θ. In some embodiments, Form IV of Compound 1 is characterized in that it has three or more peaks in its powder X-ray diffraction pattern selected from those at about 18.18, about 18.56, about 16.95, about 21.95, and about 9.85 degrees 2θ. In some embodiments, Form IV of Compound 1 is characterized in that it has four or more peaks in its powder X-ray diffraction pattern selected from those at about 18.18, about 18.56, about 16.95, about 21.95, and about 9.85 degrees 2θ. In some embodiments, Form IV of Compound 1 is characterized in that it has all five peaks in its powder X-ray diffraction pattern selected from those at about 18.18, about 18.56, about 16.95, about 21.95, and about 9.85 degrees 2θ.

In some embodiments, the present invention provides a solvated crystalline form of Compound 1 mesylate referred to as Form IV. In some embodiments, the present invention provides Form IV of Compound 1, having a powder X-ray diffraction pattern substantially similar to that depicted in FIG. 5. In some embodiments, Form IV of Compound 1 is characterized in that it has one or more peaks in its powder X-ray diffraction pattern selected from those in Table 5 below.

TABLE 5

Compound 1 Form IV XRPD Peaks

| Position (°2θ) | Height (cts) | Relative Intensity (%) |
|---|---|---|
| 9.0868 | 217.58 | 16.34 |
| 9.9380 | 112.78 | 8.47 |
| 11.2015 | 139.55 | 10.48 |
| 11.6693 | 532.94 | 40.03 |
| 12.4562 | 1116.21 | 83.84 |
| 13.5565 | 475.43 | 35.71 |
| 14.3279 | 297.10 | 22.32 |
| 16.2841 | 734.91 | 55.20 |
| 17.5789 | 573.88 | 43.11 |
| 17.7956 | 1331.34 | 100.00 |
| 18.2686 | 633.58 | 47.59 |
| 20.8156 | 206.11 | 15.48 |
| 21.2458 | 669.21 | 50.27 |
| 22.7697 | 444.50 | 33.39 |
| 22.8359 | 453.11 | 34.03 |
| 24.3821 | 1035.69 | 77.79 |
| 24.4269 | 991.19 | 74.45 |
| 25.0192 | 343.23 | 25.78 |
| 26.0048 | 819.45 | 61.55 |
| 26.3650 | 561.69 | 42.19 |
| 26.6839 | 561.23 | 42.16 |
| 28.2069 | 458.32 | 34.43 |
| 29.0196 | 498.54 | 37.45 |
| 29.4230 | 75.94 | 5.70 |

In some embodiments, Form IV of Compound 1 is characterized in that it has two or more peaks in its powder X-ray diffraction pattern selected from those in Table 5. In some embodiments, Form IV of Compound 1 is characterized in that it has three or more peaks in its powder X-ray diffraction pattern selected from those in Table 5. In some embodiments, Form IV of Compound 1 is characterized in that it has four or more peaks in its powder X-ray diffraction pattern selected from those in Table 5. In some embodiments, Form IV of Compound 1 is characterized in that it has five or more peaks in its powder X-ray diffraction pattern selected from those in Table 5. In some embodiments, Form IV of Compound 1 is characterized in that it has all of the peaks in Table 5 in its X-ray diffraction pattern.

In some embodiments, Form IV of Compound 1 is characterized in that it has one or more peaks in its powder X-ray diffraction pattern selected from those at about 17.79, about 12.45, about 24.38, about 26.00, and about 16.28 degrees 2θ. In some embodiments, Form IV of Compound 1 is characterized in that it has two or more peaks in its powder X-ray diffraction pattern selected from those at about 17.79, about 12.45, about 24.38, about 26.00, and about 16.28 degrees 2θ. In some embodiments, Form IV of Compound 1 is characterized in that it has three or more peaks in its powder X-ray diffraction pattern selected from those at about 17.79, about 12.45, about 24.38, about 26.00, and about 16.28 degrees 2θ. In some embodiments, Form IV of Compound 1 is characterized in that it has four or more peaks in its powder X-ray diffraction pattern selected from those at about 17.79, about 12.45, about 24.38, about 26.00, and about 16.28 degrees 2θ. In some embodiments, Form IV of Compound 1 is characterized in that it has all five peaks in its powder X-ray diffraction pattern selected from those at about 17.79, about 12.45, about 24.38, about 26.00, and about 16.28 degrees 2θ.

In some embodiments, the present invention provides a solvated crystalline form of Compound 1 mesylate referred to as Form V. In some embodiments, the present invention provides Form V of Compound 1, having a powder X-ray diffraction pattern substantially similar to that depicted in FIG. 6. In some embodiments, Form V of Compound 1 is characterized in that it has a peaks in its powder X-ray diffraction pattern selected from those in Table 6 below.

TABLE 6

Compound 1 Form V XRPD Peaks

| Position (°2θ) | Height (cts) | Relative Intensity (%) |
|---|---|---|
| 8.8015 | 11290.03 | 90.50 |
| 9.1530 | 1790.47 | 14.35 |
| 11.0991 | 11252.14 | 90.19 |
| 13.3400 | 12475.81 | 100.00 |
| 13.8062 | 953.33 | 7.64 |
| 14.3632 | 1444.62 | 11.58 |
| 15.9141 | 1800.60 | 14.43 |
| 16.8514 | 6543.25 | 52.45 |
| 18.1930 | 941.79 | 7.55 |
| 18.2976 | 1975.37 | 15.83 |
| 19.4061 | 686.44 | 5.50 |
| 19.9458 | 2405.91 | 19.28 |
| 22.1386 | 654.92 | 5.25 |
| 22.2572 | 2187.88 | 17.54 |
| 23.9392 | 1769.38 | 14.18 |
| 25.4909 | 5485.33 | 43.97 |
| 25.5616 | 2667.47 | 21.38 |
| 26.8123 | 4452.31 | 35.69 |
| 26.8876 | 2092.66 | 16.77 |
| 28.4313 | 785.08 | 6.29 |
| 33.5285 | 664.61 | 5.33 |

In some embodiments, Form V of Compound 1 is characterized in that it has two or more peaks in its powder X-ray diffraction pattern selected from those in Table 5. In some embodiments, Form V of Compound 1 is characterized in that it has three or more peaks in its powder X-ray diffraction pattern selected from those in Table 5. In some embodiments, Form V of Compound 1 is characterized in that it has four or more peaks in its powder X-ray diffraction pattern selected from those in Table 5. In some embodiments, Form V of Compound 1 is characterized in that it has five or more peaks in its powder X-ray diffraction pattern selected from those in Table 5. In some embodiments, Form V of Compound 1 is characterized in that it has all of the peaks in Table 5 in its X-ray diffraction pattern.

In some embodiments, Form V of Compound 1 is characterized in that it has one or more peaks in its powder X-ray diffraction pattern selected from those at about 13.34, about 8.80, about 11.10, about 16.85, and about 25.49 degrees 2θ. In some embodiments, Form V of Compound 1 is characterized in that it has two or more peaks in its powder X-ray diffraction pattern selected from those at about 13.34, about 8.80, about 11.10, about 16.85, and about 25.49 degrees 2θ. In some embodiments, Form V of Compound 1 is characterized in that it has three or more peaks in its powder X-ray diffraction pattern selected from those at about 13.34, about 8.80, about 11.10, about 16.85, and about 25.49 degrees 2θ. In some embodiments, Form V of Compound 1 is characterized in that it has four or more peaks in its powder X-ray diffraction pattern selected from those at about 13.34, about 8.80, about 11.10, about 16.85, and about 25.49 degrees 2θ. In some embodiments, Form V of Compound 1 is characterized in that it has all five peaks in its powder X-ray diffraction pattern selected from those at about 13.34, about 8.80, about 11.10, about 16.85, and about 25.49 degrees 2θ.

Compounds and Definitions:

Compounds of this invention include those described generally above, and are further illustrated by the classes, subclasses, and species disclosed herein. As used herein, the following definitions shall apply unless otherwise indicated.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, as does the Handbook of Pharmaceutical Salts: Properties, Selection, and Use, 2$^{nd}$ Revised Edition, P. Heinrich Stahl and Camille G. Wermuth, Eds. Wiley, April, 2011, each of which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include metal ions (including aluminum, zinc, alkali metals, alkaline earth metals), ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, those derived from nontoxic ammonium, quaternary ammonium, and primary, secondary or tertiary amine cations, including but not limited to those derived from natural or non-naturally-occurring amino acids. Representative amine or ammonium-based salts include but are not limited to those derived from arginine, betaine, hydrabamine, choline, diethylamine, lysine, benzathine, 2-(diethylamino)-ethanol, ethanolamine, 1-(2-hydroxyethyl)-pyrrolidine, diethanolamine, ammonia, deanol, N-methyl-glucamine, tromethamine, triethanolamine, 4-(2-hydroxyethyl)-morpholine, 1H-imidazole, ethylenediamine, piperazine, procaine, and benethamine.

3. General Methods for Providing the Present Compounds

In some embodiments, the present invention provides synthetic methods and synthetic intermediates for the production of compounds of formula I.

In some embodiments, compounds of the present invention of formula I (including, but not limited to Compound 1) can be generally prepared according to the method depicted in Scheme 1 below, wherein each of X, Y, Z, $R^E$, and $R^{PG}$ are as defined in classes and subclasses herein, both singly and in combination.

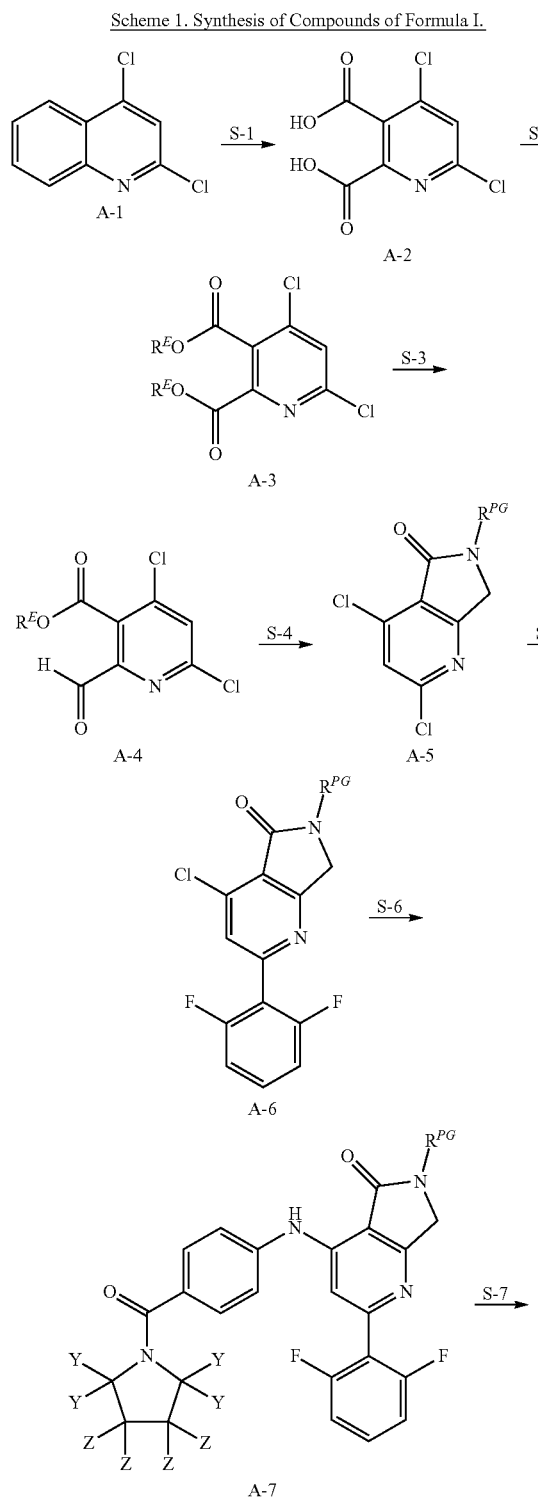

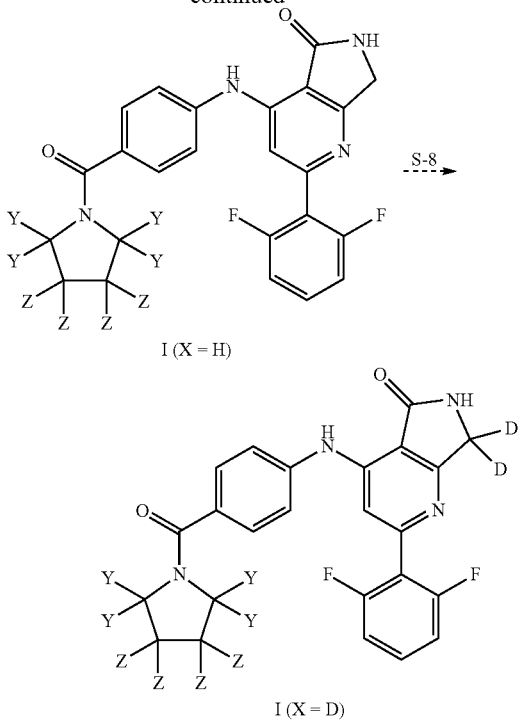

As used herein, $R^E$ is $C_{1-6}$ aliphatic group. In some embodiments, $R^E$ is a $C_{1-6}$ alkyl group. In some embodiments, $R^E$ is methyl or ethyl. In some embodiments, $R^E$ is ethyl.

As used herein, $R^{PG}$ is an amine protecting group. In some embodiments, $R^{PG}$ is an optionally substituted benzyl or benzhydryl. In some embodiments, $R^{PG}$ is an optionally substituted benzyl. In some embodiments, $R^{PG}$ is benzyl substituted by one or more methoxy groups. In some embodiments, $R^{PG}$ is 2,4-dimethoxybenzyl.

In some embodiments, step S-1 comprises the oxidation of an intermediate A-1, thereby forming an intermediate A-2. In some embodiments, the oxidation is mediated by periodate and ruthenium. In some embodiments, the periodate is sodium periodate. In some embodiments, the ruthenium is $RuCl_3$ hydrate.

In some embodiments, step S-2 comprises the esterification of a diacid intermediate A-2, thereby forming a diester intermediate A-3. In some embodiments, the esterification is base catalyzed. In some embodiments, the esterification reagent is a dialkyl sulfate. In some embodiments, the esterification reagent is diethyl sulfate. In some embodiments, the base is a carbonate base. In some embodiments, the base is potassium carbonate. In some embodiments, the esterification is performed in polar aprotic solvent. In some embodiments, the polar aprotic solvent is a cyclic urea. In some embodiments, the polar aprotic solvent is DMPU.

In some embodiments, step S-3 comprises the selective monoreduction of diester intermediate A-3 to provide an intermediate of formula A-4. In some embodiments, the selective monoreduction is accomplished with a hydride reducing agent. In some embodiments, the hydride reducing agent is an aluminum hydride. In some embodiments, the hydride reducing agent is DIBAL-H. In some embodiments, the selective monoreduction is performed in organic solvent. In some embodiments, the organic solvent is toluene. In some embodiments, the reaction is conducted at a temperature between −70 to −80° C. In some embodiments, the reaction is held at a temperature between −70 to −80° C. until A-3 is determined to be completely consumed, and then quenched at a temperature between −70 to −80° C. In some embodiments, the reagents used to quench the reaction comprise methanol. In some embodiments, the reagents used to quench the reaction comprise methanol and hydrochloric acid.

In some embodiments, step S-4 comprises the reductive cyclization of an intermediate of formula A-4 with a protected ammonia synthon to provide an intermediate of formula A-5. In some embodiments, the protected ammonia synthon is of the formula $R^{PG}$—$NH_2$. In some embodiments, the reduction is accomplished using a hydride reagent. In some embodiments, the hydride reagent is a borohydride. In some embodiments, the hydride reagent is a triacetoxyborohydride. In some embodiments, the hydride reagent is sodium triacetoxyborohydride. In some embodiments, the reaction is conducted in organic solvent. In some embodiments, the organic solvent is toluene.

In some embodiments, step S-5 comprises the aryl coupling of an intermediate of formula A-5 with a difluorophenyl synthon to provide an intermediate of formula A-6. In some embodiments, the difluorophenyl synthon is an organometallic reagent. In some embodiments, the difluorophenyl synthon is an arylzinc reagent. In some embodiments, the aryl coupling is a palladium catalyzed coupling. In some embodiments, the aryl coupling is a Negishi coupling. In some embodiments, the arylzinc reagent is prepared from the corresponding 2-bromo-1,3-difluorobenzene. In some embodiments, the 2-bromo-1,3-difluorobenzene is treated with an organometallic precursor. In some embodiments, the 2-bromo-1,3-difluorobenzene is treated with isopropylmagnesium chloride-lithium chloride complex to form an arylmagnesium lithium chloride intermediate. In some embodiments, the arylmagnesium lithium chloride intermediate is contacted with a zinc salt to form the arylzinc reagent. In some embodiments, the zinc salt is $ZnCl_2$. In some embodiments, the aryl coupling with of the intermediate of formula A-5 is catalyzed by a palladium catalyst. In some embodiments, the palladium catalyst is $Pd(PPh_3)_4$. In some embodiments, the aryl coupling is conducted in an ether solvent. In some embodiments, the ether solvent is THF.

In some embodiments, step S-6 comprises the aryl amination of an intermediate of formula A-6 with an aniline of formula A-6a:

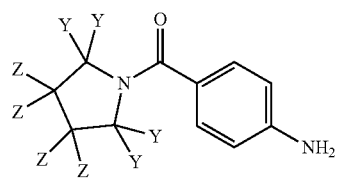

A-6a wherein Y and Z are independently hydrogen or deuterium, thereby forming an intermediate of formula A-7. In some embodiments, the aniline of formula A-6a is formed by the amination of p-aminobenzoyl chloride with the corresponding pyrrolidine of formula A6-b:

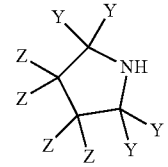

A-6b wherein Y and Z are independently hydrogen or deuterium. In some embodiments, the aryl amination is catalyzed by a palladium catalyst system. In some embodiments, the palladium catalyst system comprises $Pd_2(dba)_3$ and Xantphos. In some embodiments the aryl amination is conducted in organic solvent. In some embodiments, the organic solvent is dioxane.

In some embodiments, step S-7 comprises the removal of $R^{PG}$ from an intermediate of formula A-7, thereby forming a compound of formula I wherein X is hydrogen. In some embodiments, the removal of $R^{PG}$ comprises contacting an intermediate of formula A-7 with an acid. In some embodiments, the acid comprises a protic acid. In some embodiments, the acid comprises hydrobromic acid. In some embodiments, the acid comprises hydrobromic acid in acetic acid. In some embodiments, the reaction is conducted in an additional solvent. In some embodiments, the additional solvent is dichloromethane.

In some embodiments, step S-8 comprises the hydrogen/deuterium exchange of a compound of formula I where X is hydrogen, thereby forming a compound of formula I wherein X is deuterium. In some embodiments, the hydrogen/deuterium exchange takes place in a deuterated solvent. In some embodiments, the deuterated solvent comprises $D_2O$. In some embodiments, the deuterated solvent comprises a deuterated methanol. In some embodiments, the deuterated solvent comprises $CH_3OD$. In some embodiments, the deuterated solvent comprises $CD_3OD$. In some embodiments the deuterated solvent comprises $CDCl_3$. In some embodiments, the deuterated solvent comprises a mixture of two or more of $D_2O$, $CH_3OD$, $CD_3OD$, or $CDCl_3$. In some embodiments, the hydrogen/deuterium exchange is promoted by base. In some embodiments the base is derived from sodium metal in deuterated solvent.

Uses, Formulation and Administration and Pharmaceutically Acceptable Compositions According to another embodiment, the invention provides a composition comprising a compound of this invention or a pharmaceutically acceptable salt, ester, or salt of ester thereof and a pharmaceutically acceptable carrier, adjuvant, or vehicle. The amount of compound in compositions of this invention is such that is effective to measurably inhibit Tyk2, in a biological sample or in a patient. In certain embodiments, the amount of compound in compositions of this invention is such that is effective to measurably inhibit Tyk2, in a biological sample or in a patient. In certain embodiments, a composition of this invention is formulated for administration to a patient in need of such composition. In some embodiments, a composition of this invention is formulated for oral administration to a patient.

The term "compound" as used herein, means an Tyk2 inhibitor of Formula I (including but not limited to Compound 1), or a solid form thereof. In some embodiments, a compound is Compound 1 or a pharmaceutically acceptable salt thereof. In some embodiments, a compound is the free base of Compound 1. In some embodiments, a compound is a solid form of Compound 1. In some embodiments, a compound is a crystalline form of Compound 1. In some embodiments, a compound is Form I', Form I, Form II, Form III, Form IV, or Form V of Compound 1. In some embodiments, a compound is a polymorph of the free base of Compound 1. In some embodiments, a compound is Form I' of Compound 1. In some embodiments, a compound is a In some embodiments, a compound is a mesylate salt of Compound 1. In some embodiments, a compound is Form I of Compound 1. In some embodiments, a compound is a solvate of Compound 1. In some embodiments, a compound is amorphous Compound 1.

The term "patient," as used herein, means an animal, preferably a mammal, and most preferably a human.

The term "pharmaceutically acceptable carrier, adjuvant, or diluent" refers to a non-toxic carrier, adjuvant, or vehicle that does not destroy the pharmacological activity of the compound with which it is formulated. Pharmaceutically acceptable carriers, adjuvants or diluents that may be used in the compositions of this invention include, but are not limited to, antiadherents, binders, coatings, colorants, disintegrants, flavors, glidants, lubricants, preservatives, sorbents, and vehicles. Examples of carriers, adjuvants, and diluents include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of Tyk2.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Compositions Thereof
Pharmaceutical Uses

Compounds and compositions described herein are generally useful for the inhibition of kinase activity of one or more enzymes. In some embodiments the kinase inhibited by the compounds and methods of the invention is TYK2

TYK2 is a non-receptor tyrosine kinase member of the Janus kinase (JAKs) family of protein kinases. The mammalian JAK family consists of four members, TYK2, JAK1, JAK2, and JAK3. JAK proteins, including TYK2, are integral to cytokine signaling. TYK2 associates with the cytoplasmic domain of type I and type II cytokine receptors, as well as interferon types I and III receptors, and is activated by those receptors upon cytokine binding. Cytokines implicated in TYK2 activation include interferons (e.g. IFN-α, IFN-β, IFN-κ, IFN-δ, IFN-ε, IFN-τ, IFN-ω, and IFN-ζ (also known as limitin), and interleukins (e.g. IL-4, IL-6, IL-10, IL-11, IL-12, IL-13, IL-22, IL-23, IL-27, IL-31, oncostatin M, ciliary neurotrophic factor, cardiotrophin 1, cardiotrophin-like cytokine, and LIF). Velasquez et al., "A protein kinase in the interferon α/β signaling pathway," Cell (1992) 70:313; Stahl et al., "Association and activation of Jak-Tyk kinases by CNTF-LIF-OSM-IL-6β receptor components," Science (1994) 263:92; Finbloom et al., "IL-10 induces the tyrosine phosphorylation of Tyk2 and Jak1 and the differential assembly of Stat1 and Stat3 complexes in human T cells and monocytes," J. Immunol. (1995) 155:1079; Bacon et al., "Interleukin 12 (IL-12) induces tyrosine phosphorylation of Jak2 and Tyk2: differential use of Janus family kinases by IL-2 and IL-12," J. Exp. Med. (1995) 181:399; Welham et al., "Interleukin-13 signal transduction in lymphohemopoietic cells: similarities and differences in signal transduction with interleukin-4 and insulin," J. Biol. Chem. (1995) 270:12286; Parham et al., "A receptor for the heterodimeric cytokine IL-23 is composed of IL-12Rβ1 and a novel cytokine receptor subunit, IL-23R," J. Immunol. (2002) 168:5699. The activated TYK2 then goes on to phosphorylate further signaling proteins such as members of the STAT family, including STAT1, STAT2, STAT4, and STAT6.

TYK2 activation by IL-23, has been linked to inflammatory bowel disease (IBD), Crohn's disease, and ulcerative colitis. Duerr et al., "A Genome-Wide Association Study Identifies IL23R as an Inflammatory Bowel Disease Gene," Science (2006) 314:1461-1463. As the downstream effector of IL-23, TYK2 also plays a role in psoriasis, ankylosing spondylitis, and Behçet's disease. Cho et al., "Genomics and the multifactorial nature of human auto-immune disease," N. Engl. J. Med (2011) 365:1612-1623; Cortes et al., "Identification of multiple risk variants for ankylosing spondylitis through high-density genotyping of immune-related loci," Nat. Genet. (2013) 45(7):730-738; Remmers et al., "Genome-wide association study identifies variants in the MHC class I, IL10, and IL23R-IL12RB2 regions associated with Behçet's disease," Nat. Genet. (2010) 42:698-702. A genome-wide association study of 2,622 individuals with psoriasis identified associations between disease susceptibility and TYK2. Strange et al., "A genome-wide association study identifies new psoriasis susceptibility loci and an interaction between HLA-C and ERAP1," Nat. Genet. (2010) 42:985-992. Knockout or tyrphostin inhibition of TYK2 significantly reduces both IL-23 and IL-22-induced dermatitis. Ishizaki et al., "Tyk2 is a therapeutic target for psoriasis-like skin inflammation," Intl. Immunol. (2013), doi: 10.1093/intimm/dxt062.

TYK2 also plays a role in respiratory diseases such as asthma, chronic obstructive pulmonary disease (COPD), lung cancer, and cystic fibrosis. Goblet cell hyperplasia (GCH) and mucous hypersecretion is mediated by IL-13-induced activation of TYK2, which in turn activates STAT6. Zhang et al., "Docking protein Gab2 regulates mucin expression and goblet cell hyperplasia through TYK2/STAT6 pathway," FASEB J. (2012) 26:1-11.

Decreased TYK2 activity leads to protection of joints from collagen antibody-induced arthritis, a model of human rheumatoid arthritis. Mechanistically, decreased Tyk2 activity reduced the production of $T_h1/T_h17$-related cytokines and matrix metalloproteases, and other key markers of inflammation. Ishizaki et al., "Tyk2 deficiency protects joints against destruction in anti-type II collagen antibody-induced arthritis in mice," Intl. Immunol. (2011) 23(9):575-582.

TYK2 knockout mice showed complete resistance in experimental autoimmune encephalomyelitis (EAE, an animal model of multiple sclerosis (MS)), with no infiltration of CD4 T cells in the spinal cord, as compared to controls, suggesting that TYK2 is essential to pathogenic CD4-mediated disease development in MS. Oyamada et al., "Tyrosine Kinase 2 Plays Critical Roles in the Pathogenic CD4 T Cell Responses for the Development of Experimental Autoimmune Encephalomyelitis," J. Immunol. (2009) 183: 7539-7546. This corroborates earlier studies linking increased TYK2 expression with MS susceptibility. Ban et al., "Replication analysis identifies TYK2 as a multiple sclerosis susceptibility factor," Eur J. Hum. Genet. (2009) 17:1309-1313. Loss of function mutation in TYK2, leads to decreased demyelination and increased remyelination of neurons, further suggesting a role for TYK2 inhibitors in the treatment of MS and other CNS demyelination disorders.

TYK2 is the sole signaling messenger common to both IL-12 and IL-23. TYK2 knockout reduced methylated BSA injection-induced footpad thickness, imiquimod-induced psoriasis-like skin inflammation, and dextran sulfate sodium or 2,4,6-trinitrobenzene sulfonic acid-induced colitis in mice.

Joint linkage and association studies of various type I IFN signaling genes with systemic lupus erythematosus (SLE, an autoimmune disorder), showed a strong, and significant correlation between loss of function mutations to TYK2 and decreased prevalence of SLE in families with affected members. Sigurdsson et al., "Polymorphisms in the Tyrosine Kinase 2 and Interferon Regulatory Factor 5 Genes Are Associated with Systemic Lupus Erythematosus," Am. J. Hum. Genet. (2005) 76:528-537. Genome-wide association studies of individuals with SLE versus an unaffected cohort showed highly significant correlation between the TYK2 locus and SLE. Graham et al., "Association of NCF2, IKZF1, IRF8, IFIH1, and TYK2 with Systemic Lupus Erythematosus," PLoS Genetics (2011) 7(10):e1002341.

TYK2 has been shown to play an important role in maintaining tumor surveillance and TYK2 knockout mice showed compromised cytotoxic T cell response, and accelerated tumor development. However, these effects were linked to the efficient suppression of natural killer (NK) and cytotoxic T lymphocytes, suggesting that TYK2 inhibitors would be highly suitable for the treatment of autoimmune disorders or transplant rejection. Although other JAK family members such as JAK3 have similar roles in the immune system, TYK2 has been suggested as a superior target because of its involvement in fewer and more closely related signaling pathways, leading to fewer off-target effects. Simma et al. "Identification of an Indispensable Role for Tyrosine Kinase 2 in CTL-Mediated Tumor Surveillance," Cancer Res. (2009) 69:203-211.

However, paradoxically to the decreased tumor surveillance observed by Simma et al., studies in T-cell acute lymphoblastic leukemia (T-ALL) indicate that T-ALL is highly dependent on IL-10 via TYK2 via STAT1-mediated signal transduction to maintain cancer cell survival through upregulation of anti-apoptotic protein BCL2. Knockdown of TYK2, but not other JAK family members, reduced cell growth. Specific activating mutations to TYK2 that promote cancer cell survival include those to the FERM domain (G36D, S47N, and R425H), the JH2 domain (V731II), and the kinase domain (E957D and R1027H). However, it was also identified that the kinase function of TYK2 is required for increased cancer cell survival, as TYK2 enzymes featuring kinase-dead mutations (M978Y or M978F) in addition to an activating mutation (E957D) resulted in failure to transform. Sanda et al. "TYK2-STAT1-BCL2 Pathway Dependence in T-Cell Acute Lymphoblastic Leukemia," Cancer Disc. (2013) 3(5):564-577.

Thus, selective inhibition of TYK2 has been suggested as a suitable target for patients with IL-10 and/or BCL2-addicted tumors, such as 70% of adult T-cell leukemia cases. Fontan et al. "Discovering What Makes STAT Signaling TYK in T-ALL," Cancer Disc. (2013) 3:494-496.

TYK2 mediated STAT3 signaling has also been shown to mediate neuronal cell death caused by amyloid-β (Aβ) peptide. Decreased TYK2 phosphorylation of STAT3 following Aβ administration lead to decreased neuronal cell death, and increased phosphorylation of STAT3 has been observed in postmortem brains of Alzheimer's patients. Wan et al. "Tyk/STAT3 Signaling Mediates β-Amyloid-Induced Neuronal Cell Death: Implications in Alzheimer's Disease," J. Neurosci. (2010) 30(20):6873-6881.

Inhibition of JAK-STAT signaling pathways is also implicated in hair growth, and the reversal of the hair loss associated with alopecia areata. Xing et al., "Alopecia areata is driven by cytotoxic T lymphocytes and is reversed by JAK inhibition," Nat. Med. (2014) 20: 1043-1049; Harel et al., "Pharmacologic inhibition of JAK-STAT signaling promotes hair growth," Sci. Adv. (2015) 1(9):e1500973.

Accordingly, compounds that inhibit the activity of TYK2 are beneficial, especially those with selectivity over JAK2. Such compounds should deliver a pharmacological response that favorably treats one or more of the conditions described herein without the side-effects associated with the inhibition of JAK2.

Even though TYK2 inhibitors are known in the art, there is a continuing need to provide novel inhibitors having more effective or advantageous pharmaceutically relevant properties. For example, compounds with increased activity, selectivity over other JAK kinases (especially JAK2), and ADMET (absorption, distribution, metabolism, excretion, and/or toxicity) properties. Thus, in some embodiments, the present invention provides inhibitors of TYK2 which show selectivity over JAK2.

The activity of a compound utilized in this invention as an inhibitor of TYK2, or a mutant thereof, may be assayed in vitro, in vivo or in a cell line. In vitro assays include assays that determine inhibition of either the phosphorylation activity and/or the subsequent functional consequences, or ATPase activity of activated TYK2, or a mutant thereof. Alternate in vitro assays quantitate the ability of the inhibitor to bind to TYK2. Inhibitor binding may be measured by radiolabeling the inhibitor prior to binding, isolating the inhibitor/TYK2 complex and determining the amount of radiolabel bound. Alternatively, inhibitor binding may be determined by running a competition experiment where new inhibitors are incubated with TYK2 bound to known radioligands. Representative in vitro and in vivo assays useful in assaying a TYK2 inhibitor include those described and disclosed in, e.g., each of which is herein incorporated by reference in its entirety. Detailed conditions for assaying a compound utilized in this invention as an inhibitor of TYK2, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of TYK2 and are therefore useful for treating one or more disorders associated with activity of TYK2 or mutants thereof. Thus, in certain embodiments, the present invention provides a method for treating a TYK2-mediated disorder comprising the step of administering to a patient in need thereof a compound of the present invention, or pharmaceutically acceptable composition thereof.

As used herein, the term "TYK2-mediated" disorders, diseases, and/or conditions as used herein means any disease or other deleterious condition in which TYK2 or a mutant thereof is known to play a role. Accordingly, another embodiment of the present invention relates to treating or lessening the severity of one or more diseases in which TYK2, or a mutant thereof, is known to play a role. Such TYK2-mediated disorders include but are not limited to autoimmune disorders, inflammatory disorders, proliferative disorders, endocrine disorders, neurological disorders and disorders associated with transplantation.

In some embodiments, the present invention provides a method for treating one or more disorders, wherein the disorders are selected from autoimmune disorders, inflammatory disorders, proliferative disorders, endocrine disorders, neurological disorders, and disorders associated with transplantation, said method comprising administering to a patient in need thereof, a pharmaceutical composition comprising an effective amount of a compound of the present invention, or a pharmaceutically acceptable salt thereof.

In some embodiments, the disorder is an autoimmune disorder. In some embodiments the disorder is selected from type 1 diabetes, systemic lupus erythematosus, multiple sclerosis, psoriasis, Behçet's disease, POEMS syndrome, Crohn's disease, ulcerative colitis, and inflammatory bowel disease.

In some embodiments, the disorder is an inflammatory disorder. In some embodiments, the inflammatory disorder is rheumatoid arthritis, asthma, chronic obstructive pulmonary disease, psoriasis, hepatomegaly, Crohn's disease, ulcerative colitis, inflammatory bowel disease.

In some embodiments, the disorder is a proliferative disorder. In some embodiments, the proliferative disorder is a hematological cancer. In some embodiments the proliferative disorder is a leukemia. In some embodiments, the leukemia is a T-cell leukemia. In some embodiments the T-cell leukemia is T-cell acute lymphoblastic leukemia (T-ALL). In some embodiments the proliferative disorder is polycythemia vera, myelofibrosis, essential or thrombocytosis.

In some embodiments, the disorder is an endocrine disorder. In some embodiments, the endocrine disorder is polycystic ovary syndrome, Crouzon's syndrome, or type 1 diabetes.

In some embodiments, the disorder is a neurological disorder. In some embodiments, the neurological disorder is Alzheimer's disease.

In some embodiments the proliferative disorder is associated with one or more activating mutations in TYK2. In some embodiments, the activating mutation in TYK2 is a mutation to the FERM domain, the JH2 domain, or the kinase domain. In some embodiments the activating mutation in TYK2 is selected from G36D, S47N, R425H, V731I, E957D, and R1027H.

In some embodiments, the disorder is associated with transplantation. In some embodiments the disorder associated with transplantation is transplant rejection, or graft versus host disease.

In some embodiments the disorder is associated with type I interferon, IL-10, IL-12, or IL-23 signaling. In some embodiments the disorder is associated with type I interferon signaling. In some embodiments the disorder is associated with IL-10 signaling. In some embodiments the disorder is associated with IL-12 signaling. In some embodiments the disorder is associated with IL-23 signaling.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin Associated Periodic Syndrome (CAPS), and osteoarthritis.

In some embodiments the inflammatory disease which can be treated according to the methods of this invention is a $T_h1$ or $T_h17$ mediated disease. In some embodiments the $T_h17$ mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Furthermore, the invention provides the use of a compound according to the definitions herein, or a pharmaceutically acceptable salt, or a hydrate or solvate thereof for the preparation of a medicament for the treatment of an autoimmune disorder, an inflammatory disorder, or a proliferative disorder, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporine, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmicort®), and flunisolide (Aerobid®), Afviar®, Symbicort®, Dulera®, cromolyn sodium (Intal®), methylxanthines such as theophylline (Theo-Dur®, Theolair®, Slo-Bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevirapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating systemic lupus erythematosus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmicort®), flunisolide (Aerobid®), Afviar®, Symbicort®, and Dulera®, cromolyn sodium (Intal®), methylxanthines such as theophylline (Theo-Dur®, Theolair®, Slo-Bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-Bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmicort®), flunisolide (Aerobid®), Afviar®, Symbicort®, and Dulera®, In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et a! "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behçet's disease, scleroderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphigus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

In some embodiments, the present invention provides a method of treating or lessening the severity of a disease, comprising administering to a patient in need thereof a TYK2 pseudokinase (JH2) domain binding compound and a TYK2 kinase (JH1) domain binding compound. In some embodiments, the disease is an autoimmune disorder, an inflammatory disorder, a proliferative disorder, an endocrine disorder, a neurological disorder, or a disorder associated with transplantation. In some embodiments the JH2 binding compound is a compound of formula I. Other suitable JH2 domain binding compounds include those described in WO2014074660A1, WO2014074661A1, WO2015089143A1, the entirety of each of which is incorporated herein by reference. Suitable JH1 domain binding compounds include those described in WO2015131080A1, the entirety of which is incorporated herein by reference.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting TYK2, or a mutant thereof, activity in a biological sample comprising the step of contacting said biological sample with a compound of this invention, or a composition comprising said compound. In certain embodiments, the invention relates to a method of irreversibly inhibiting TYK2, or a mutant thereof, activity in a biological sample comprising the step of contacting said biological sample with a compound of this invention, or a composition comprising said compound.

In another embodiment, the invention provides a method of selectively inhibiting TYK2 over one or more of JAK1, JAK2, and JAK3. In some embodiments, a compound of the present invention is more than 2-fold selective over JAK1/2/3. In some embodiments, a compound of the present invention is more than 5-fold selective over JAK1/2/3. In some embodiments, a compound of the present invention is more than 10-fold selective over JAK1/2/3. In some embodiments, a compound of the present invention is more than 50-fold selective over JAK1/2/3. In some embodiments, a compound of the present invention is more than 100-fold selective over JAK1/2/3.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of TYK2 (or a mutant thereof) activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of TYK2, or a mutant thereof, in a patient comprising the step of administering to said patient a compound of the present invention, or a composition comprising said compound. According to certain embodiments, the invention relates to a method of reversibly or irreversibly inhibiting one or more of TYK2, or a mutant thereof, activity in a patient comprising the step of administering to said patient a compound of the present invention, or a composition comprising said compound. In other embodiments, the present invention provides a method for treating a disorder mediated by TYK2, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed, under the trade name Zavedos™. Mitoxantrone is marketed under the trade name Novantron.

The term "microtubule active agent" relates to microtubule stabilizing, microtubule destabilizing compounds and microtubulin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; colchicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD 180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; ilmofosine; RO 318220 and RO 320432; GO 6976; Isis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, S-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as cotherapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclomethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID, Apremilast (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate. In some embodiments, a compound or composition according to the present invention is administered together with Apremilast, in the same composition, or in a different pharmaceutical composition.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and terfenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H- benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent. The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds and solid forms are prepared according to the preceding general procedures. It will be appreciated that, although the general methods depict the synthesis of certain compounds of the present invention, the following methods, and other methods known to one of ordinary skill in the art, can be applied to all compounds and subclasses and species of each of these compounds, as described herein.

EXPERIMENTAL PROCEDURES:

Example 1

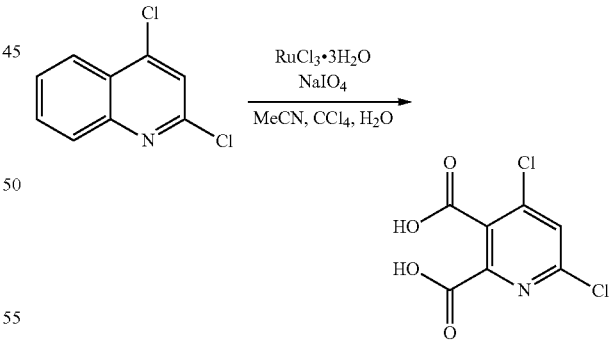

Sodium periodate (10.4 kg, 12.0 eq.), acetonitrile (8 L, 10 V), carbon tetrachloride (8 L, 10 V), and water (12 L, 15 V) were charged into a 50 L reactor. Ruthenium chloride trihydrate (4.9 g, 0.6% eq.) was added and the mixture stirred for 30 minutes at 25° C. 2,4-dichloroquinoline (800 g, 1.0 eq.) was added in portions over 60 minutes at 25° C., then the mixture was stirred vigorously for 24 hours at that temperature. Upon complete consumption of starting quinoline, the mixture was filtered and the filter cake washed with 34 L hot ethyl acetate. The aqueous layer was separated and extracted with 13 L hot ethyl acetate, the organic layers were combined and dried over anhydrous sodium sulfate, then filtered, evaporated under vacuum at 50° C. The residue was triturated with 4.8 L dichloromethane, and the solids formed were filtered and dried under vacuum yielding the product A-2 (1153 g, 97.2% yield) as an off-white solid.

Example 2

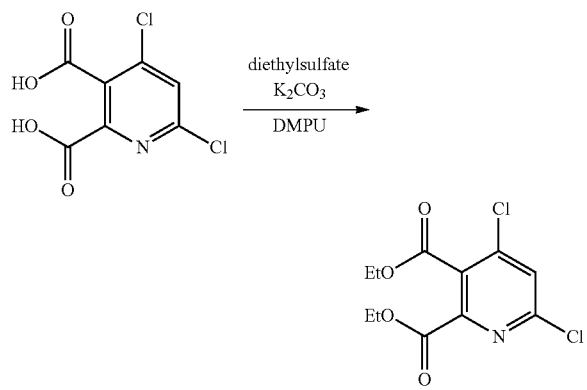

Diacid A-2 (1153 g, 1.0 eq.) from the previous step and DMPU (8 L, 7 V) were charged into a 20 L reactor and the mixture was heated to 85° C. for one hour. Potassium carbonate (1553 g, 2.3 eq.) was added in two lots over 10 minutes and the mixture was stirred for 20 minutes at 85° C. Diethyl sulfate (1.73 L, 4.3 eq.) was added over 90 minutes, maintaining the temperature between 80-90° C., and the mixture stirred for another 10 hours at that temperature. Once the starting diacid and monoester was determined by LC-MS to be present at less than 2%, the mixture was cooled to room temperature over 50 minutes, then further cooled to 0° C. Water (17 L, 15 V) and heptane (11.5 L, 10 V) were added, and the aqueous and organic layers were allowed to separate. The aqueous layer was extracted twice with heptane (11.5 L then 6 L), and the combined organic layers were washed with brine (11.5 L), then concentrated under vacuum at 50° C., yielding the diester product as an oil (1112 g, 78% yield).

Example 3

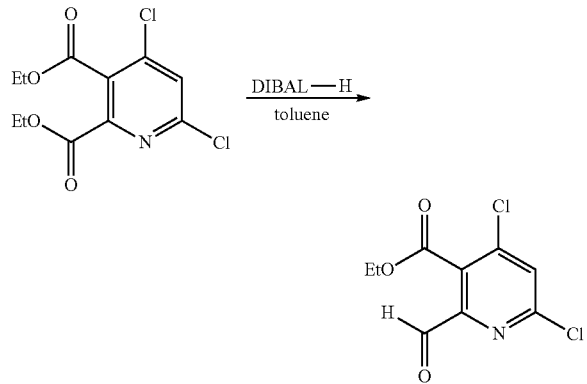

The diester from Example 2 (500 g, 1.0 eq.) and toluene (10 L, 20 V) were charged into a 20 L reactor and cooled to −78° C. DIBAL-H (1M in toluene, 3 L, 1.75 eq.) was added dropwise to the reactor over 70 minutes, maintaining the temperature between −80 and −70° C., then the mixture was stirred at that temperature for an additional 20 minutes. Upon complete consumption of starting material by TLC, methanol (1 L, 2 V) was added dropwise over 40 minutes maintaining the temperature between −80 and −70° C. 4 N HCl (400 mL, 8 V) was added dropwise over 30 minutes to the above reaction mixture, keeping the temperature below −50° C. The reaction was allowed to warm to room temperature and the aqueous layer was separated and extracted with toluene (2.5 L, 5 V). The organic layers were combined, dried over anhydrous sodium sulfate, then concentrated under vacuum at 50° C. to yield 7.5 L of solution which was used directly in the next step.

Example 4

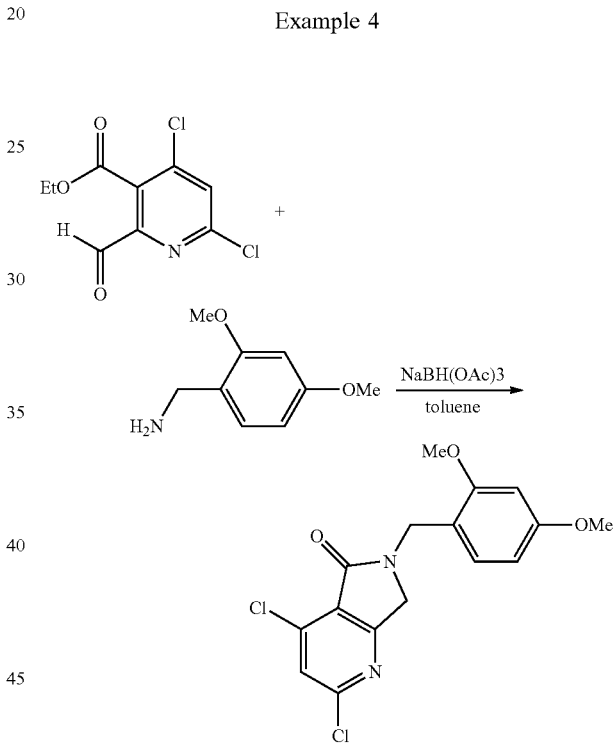

The solution of aldehyde in toluene from Example 3 (7.5 L, 1.0 eq.) was added to a 10 L reactor and cooled to 0° C. 2,4-dimethoxybenzylamine (286 g, 1.0 eq.) was added dropwise to the reactor over 20 minutes, maintaining the temperature between 0 and 10° C. Sodium triacetoxyborohydride (544.5 g, 1.5 eq.) was added to the reactor in portions over 50 minutes, and the mixture was stirred for 3 hours at room temperature. Upon complete consumption of starting material by TLC, 1 N NaOH (aq.) was added until the pH was between 6-7, followed by saturated $Na_2CO_3$ (aq.) until the pH was between 9-10. The aqueous layer was separated and washed with ethyl acetate (2×5 L), and the combined organic layers were washed with brine (1.25 L) and dried over anhydrous sodium sulfate, then concentrated under vacuum at 50° C. to give the crude product. The crude product was dissolved in acetonitrile (6 L) at 80° C. to obtain a clear solution, which was cooled to 0° C. over 2 hours, then stirred an additional hour. The solids formed were collected by filtration and dried under vacuum at 50° C. to yield the desired product (1.57 kg, 65% yield over two steps, 98.9% purity).

Example 5

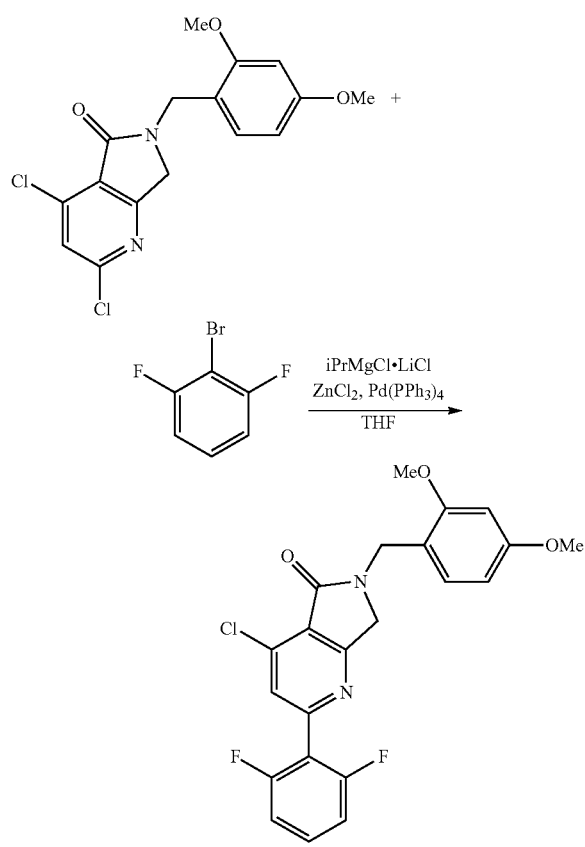

2-bromo-1,3-difluorobenzene (700 g, 1.6 eq.) and THF (8 L, 10 V) were charged into a 20 L reactor and cooled to −78° C. Isopropylmagnesium chloride-lithium chloride complex in THF (4 L, 2.3 eq.) was added dropwise to the reactor over 2 hours, maintaining the temperature between −80 and −70° C., and the mixture was stirred at that temperature until TLC analysis indicated that the starting 2-bromo-1,3-difluorobenzene was completely consumed. Zinc chloride (1.5 kg, 4.8 eq.) was added to the reactor in a single lot and stirred for 30 minutes at a temperature between −80 and −70° C., then warmed to 0° C. Pd(PPh$_3$)$_4$ (131 g, 0.05 eq.) was added to the reactor followed by the product from Example 4 (800 g, 1.0 eq.), and the mixture was stirred at room temperature for 15 hours, whereupon the dichloropyridine starting material was determined to be completely consumed by HPLC. The mixture was cooled to 0° C., and saturated aqueous NH$_4$Cl (8 L, 10 V) was added dropwise to the reactor over 1 hour, and the mixture was stirred for 30 minutes then filtered. The aqueous solution was extracted twice with 8 L ethyl acetate, and the combined organic layers were washed with brine (4 L), dried over anhydrous sodium sulfate, then concentrated under vacuum at 50° C. to give the crude product. This crude product was combined with the crude product from a separate batch employing 900 g of the product from Example 4 and triturated with MTBE (34 L) and filtered, then the solids were charged to a 20 L reactor with 3.8 L acetonitrile and stirred for 1 hour at room temperature. MTBE (9.5 L) was added dropwise for 1 hour at room temperature and stirred for an additional hour. The solids were collected by filtration and dried at room temperature to provide 1.1 kg of the desired product with 97% purity. The mother liquor from the purifications was evaporated and purified by silica gel chromatography (ethyl acetate 33 to 55% gradient in petroleum ether) to yield an additional 550 g of crude product which was dissolved in acetonitrile (500 mL) and precipitated by dropwise addition of MTBE (1500 mL). The solids formed were collected by filtration and dried to provide an additional 430 g of product with 100% purity.

Example 6

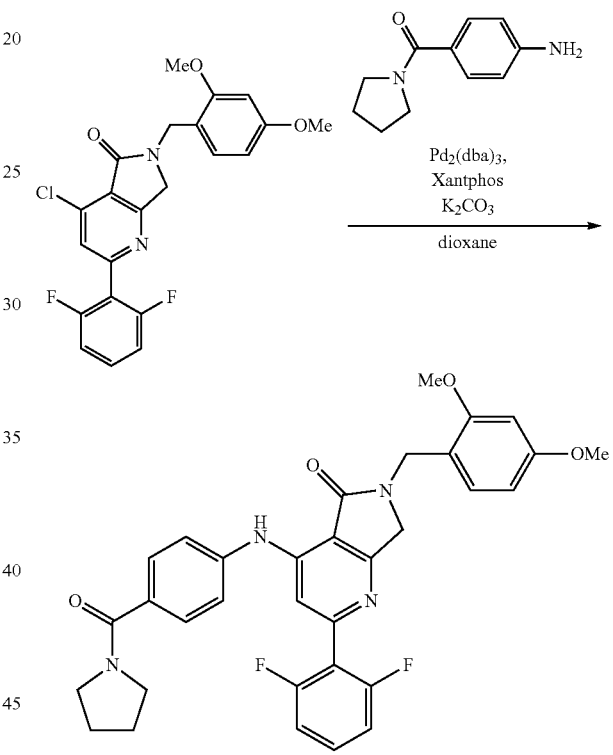

The product from Example 5 (500 g, 1.0 eq.) and N-(p-aminobenzoyl)pyrrolidine (224 g, 1.0 eq.), potassium carbonate (400 g, 2.5 eq.), and 1,4-dioxane (12.5 L, 25 V) were added to a 20 L reactor and stirred for 30 minutes while being degassed with a stream of nitrogen gas. Pd$_2$(dba)$_3$ (72.2 g, 0.06 eq.) and Xantphos (80.6 g, 0.12 eq.) were added to the reactor and the mixture was stirred for 10 minutes at room temperature, then heated to 100° C. and stirred for 15 hours, whereupon the chloropyridine starting material was determined to be completely consumed by HPLC. The mixture was filtered and water (12.5 L) was added to the filtrate, then the mixture was extracted twice with 5 L of ethyl acetate. The organic layers were combined and washed four times with 0.15 N aqueous citric acid (5 L each), once with saturated aqueous sodium bicarbonate (2.5 L) and once with brine (2.5 L), then dried over anhydrous sodium sulfate and concentrated under vacuum at 50° C. to provide the crude product as a solid. The crude solid was slurried with acetonitrile (2 V) and MTBE (10 V) for 30 minutes at room temperature, and the resulting solids were filtered and dried to provide the desired compound in 95% purity. The compound could be further purified to 98.6% purity by repeating the acetonitrile/MTBE slurrying process.

Example 7

Compound 1 Free Base

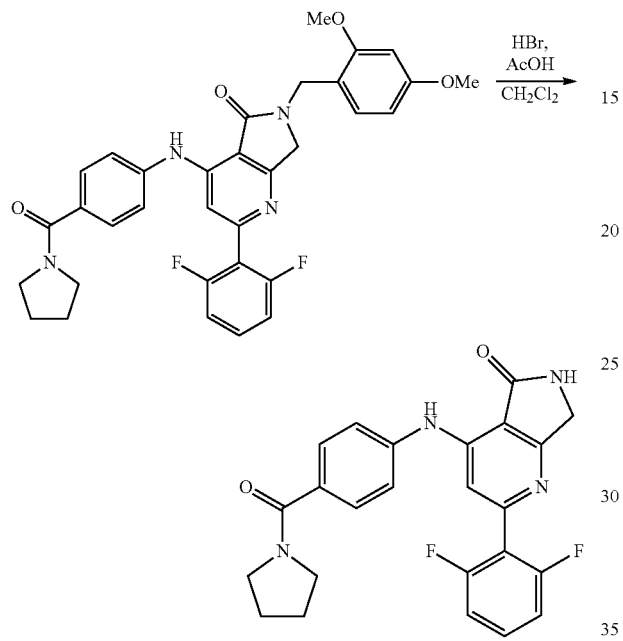

The product from Example 6 (1.2 kg, 1.0 eq.) and dichloromethane (12 L, 10 V) were charged into a 20 L reactor. Hydrobromic acid (33% in acetic acid, 7.2 L, 6 V) was added to the reactor under nitrogen atmosphere at between 20-30° C., and stirred for 15 hours at room temperature, whereupon the dimethoxybenzyl starting material was determined to be completely consumed by HPLC. The solution was cooled to between 0-10° C. and 2 N aqueous sodium hydroxide was added until the pH was greater than 2, then solid sodium bicarbonate powder was added until the pH was between 8 and 9. The mixture was filtered and the filtrate was extracted twice with dichloromethane (12 L), and the organic layers were combined, washed with brine (20 L), and dried over anhydrous sodium sulfate, then filtered and concentrated under vacuum at 40° C. to give the crude product (1.5 kg, 95% purity). The crude solid was charged into a 20 L reactor with dichloromethane (3 L) and MTBE (7.5 L), and the mixture was stirred overnight between 20-30° C. The resulting solids were collected by filtration and dried at 50° C. to a constant weight (800 g, 97% purity). This intermediate purity product was dissolved in 32 L dichloromethane with warming to 30° C. and the solution filtered. The filtrate was concentrated under vacuum at 50° C. until 3 volumes remained, then cooled to room temperature. The solids formed were collected and dried at 50° C. to constant weight (700 g, 98.7% purity). The product was dissolved in 32 L dichloromethane at 30° C. and SiliaMetS (30% w/w) was added and the mixture heated to reflux overnight, then cooled to room temperature. The mixture was filtered and the filtrate was again treated with SiliaMetS (30% w/w) and heated to reflux overnight, then cooled to room temperature. The mixture was filtered and the filtrate concentrated under vacuum at 30-40° C. MTBE (5 V) was added to the residue and stirred for 1 hour at room temperature. The solids formed were collected by filtration, dried under vacuum at 70° C. to constant weight to obtain 575 g of Compound 1 free base (99.5% purity). This material was determined to be Form I' of Compound 1 free base, having the XRPD pattern depicted in FIG. 1. Amorphous Compound 1 free base was prepared by dissolving Form I' in dichloromethane followed by rapid evaporation.

Example 8

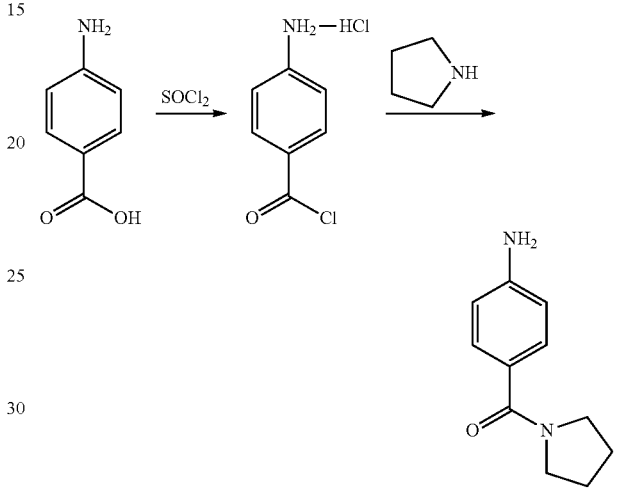

p-Aminobenzoic acid (700 g, 1.0 eq.) and thionyl chloride (4 L, 13 eq.) were charged into a 20 L reactor and stirred overnight at 50-60° C., then concentrated under vacuum at 50° C. to provide the crude acid chloride which was used without further purification. Pyrrolidine (1300 g, 5 eq.) and dichloromethane (3.5 L, 5V) were charged into a 20 L reactor and the mixture was cooled to 0° C. The acid chloride in dichloromethane (3.5 L, 5 V) was added dropwise to the reactor at 0-5° C. Once the reaction was determined to be complete by HPLC, water (7 L) was added, and the mixture was filtered. The filter cake was washed with dichloromethane (1.4 L) and water (2.8 L). The aqueous phase was separated and extracted with dichloromethane (7 L), and the organic layers were combined, then washed with brine (3.5 L) and dried over anhydrous sodium sulfate, then concentrated under vacuum at 50° C. to give the crude product. The crude was stirred overnight in n-heptane: dichloromethane (5:1, 3.5 L) overnight at room temperature, then the solids collected by filtration. The filter cake was washed with dichloromethane (1.4 L) and water (2.8 L) and both filter cakes were combined, then stirred with dichloromethane (2.8 L) overnight at 35-40° C., then cooled to 15° C. and stirred for 4 hours. The solids were collected by filtration and dried under vacuum at 50° C. to constant weight to provide the desired product (660 g, 99% purity). Deuterated analogs (i.e. those where Y and or Z is D) were prepared by the same procedure using the corresponding deuterated pyrrolidine.

Example 9

Form I and Amorphous Compound 1 Mesylate

Compound 1 free base (418.5 mg, 0.963 mmol) was dissolved in THF (15 mL) at 60° C. with stirring. To this mixture, neat methanesulfonic acid (62.6 uL, 0.963 mmol) was added in a dropwise manner over 5 minutes, resulting in the precipitation of a cream colored solid. Heating was maintained for 30 minutes, then the mixture was cooled to room temperature and filtered, washed with cold isopropanol and dried under vacuum. This material was determined to be Form I of Compound 1 mesylate having the XRPD pattern depicted in FIG. 2. The material was redissolved in 50% 1,4-dioxane in water and lyophilized to provide amorphous Compound 1 mesylate.

Example 10

Production of Form II of Compound 1 Mesylate

Amorphous Compound 1 mesylate (10 mg) was dissolved in 95% acetonitrile, 5% water (% v/v) and left to evaporate for a week. The crystalline material produced was found to be Form II of Compound 1 mesylate, having the XRPD pattern depicted in FIG. 3.

Example 11

Production of Form III and Form IV of Compound 1 Mesylate

Amorphous Compound 1 mesylate (10 mg) was dissolved in N,N'-dimethylformamide to form a saturated solution, which was subjected to crash cooling at −20° C., resulting in the formation of a crystalline solid. This material was found to be Form III of Compound 1 mesylate having the XRPD pattern depicted in FIG. 4. Upon drying under ambient conditions, Form III was found to transition to Form IV of Compound 1 mesylate having the XRPD pattern depicted in FIG. 5. Form IV was found to be stable at ambient conditions.

Example 12

Production of Form V of Compound 1 Mesylate

Amorphous Compound 1 mesylate (10 mg) was dissolved in 50% dioxane in water (% v/v) and left to evaporate for a week. The crystalline material formed was found to be Form V of Compound 1 mesylate, having the XRPD pattern depicted in FIG. 6. Upon grinding, Form V was found to transition to Form I.

Example 13

X-Ray Powder Diffraction (XRPD) Analytical Method

XRPD analysis of Forms I', I, II, III, IV, and V of Compound 1 was carried out on a PANalytical X'pert Pro diffractometer. The material was gently ground to release any agglomerates and loaded onto a multi-well plate with Kapton or Mylar polymer film to support the sample. The multi-well plate was then placed into the diffractometer and analyzed using Cu K radiation ($\alpha_1 \lambda$=1.54060 Å; $\alpha_2$ 1.54443 Å; $\beta$−1.39225 Å; $\alpha_1$:$\alpha_2$ ratio=0.5), running in transmission mode (step size 0.0130° 2θ) using 40 kV/40 mA generator settings, starting the scan at 3.0100° 2θ and ending at 35.0100° 2θ.

Example 14

Tyk2 Radioactive Kinase Assay

Peptide substrate, [KKSRGDYMTMQIG], (20 µM) is prepared in reaction buffer (20 mM Hepes pH 7.5, 10 mM MgCl2, 1 mM EGTA, 0.02% Brij35, 0.02 mg/mL BSA, 0.1 mM Na3PO4, 2 mM DTT, 1% DMSO. TYK2 (Invitrogen) kinase is added, followed by compounds in DMSO. 33PATP is added to initiate the reaction in ATP at 10 µM. Kinase reaction is incubated for 120 min at room temp and reactions are spotted onto P81 ion exchange paper (Whatman #3698-915), and then washed extensively in 0.75% phosphoric acid, prior to reading the radioactivity counts.

Compound 1, and its isotopologs 2, 3, 4, and 5 each provided an $IC_{50}$ value of less than 1 nM for the Tyk2 Radioactive Kinase Assay.

Example 15

IL-12 Induced pSTAT4 in Human PBMC

Human PBMC are isolated from buffy coat and are stored frozen for assays as needed. Cells for assay are thawed and resuspended in complete media containing serum, then cells are diluted to 1.67 E6 cells/ml so that 120 µl per well is 200,000 cells. 15 µl of compound or DMSO is added to the well at the desired concentrations and incubated at 1 hr at 37 C. 15 µl of stimulus (final concentration of 1.7 ng/mL IL-12) is added for 30 minutes prior to pSTAT4 and total STAT4 analysis using cell lysates prepared and analyzed by MSD reagents as per manufacturer protocol. The final DMSO concentration of compound in the assay is 0.1%.

Compound 1, and its isotopologs 2, 3, 4, and 5 each provided an $IC_{50}$ value of less than 150 nM for the IL-12 Induced pSTAT4 assay in human PBMC.

Example 16

CACO-2 Cell Permeability Assay

Caco-2 cells were diluted to 6.86×10 5 cells/mL with culture medium and 50 µL of cell suspension were dispensed into the filter well of the 96-well HTS Transwell plate. Cells were cultivated for 14~18 days in a cell culture incubator at 37° C., 5% C02, 95% relative humidity. Cell culture medium was replaced every 2 days, beginning no later than 24 hours after initial plating. 3) After 14~18 days incubation, the plates were removed from incubator. The inserts were washed twice with pre-warmed HBSS (10 mM HEPES, pH 7.4) and placed into receiver plates. 75 µL and 235 µL of buffer were added to each Transwell inserts and receiver wells, respectively. Then the plates were incubated for 30 min at 37° C. with shaking at 150 rpm. Stock solutions of control compound were prepared in DMSO at 10 mM and then diluted to 1 mM with DMSO followed by further diluting with HBSS (10 mM HEPES, pH 7.4) to get compound working solution. Stock solutions of test compound were prepared in DMSO at 10 mM and then diluted to 1 mM with DMSO followed by further diluting with HBSS (10 mM HEPES, pH 7.4, 4% BSA) to get compound working solution. The final concentration of test compound and control compound was 5 µM. To determine the rate of drug transport in the apical to basolateral direction, 75 µL of compound working solution was added to the filter well (apical compartment) and 235 µL of HBSS (10 mM HEPES, pH 7.4, or 4% BSA) to receiver plate (basolateral compartment). To determine the rate of drug transport in the basolateral to apical direction, 235 µL of compound working solution was added to each well of the receiver plate (basolateral compartment) and 75 µL of HBSS (10 mM HEPES, pH 7.4, or 4% BSA) to filter well (apical compartment). The assay was performed in duplicate. 6) Plates were incubated for 2 hours at 37° C. At the end of the transport period, aliquots of 50 µL were removed directly from the apical and basolateral wells and transferred to wells of new plates. Four volumes of cold Methanol containing internal standards (IS, 100 nM Alprazolam, 200 nM Labetalol and 200 nM Diclofenac) was added into each well. Samples were centrifuged at 3,220 g for 30 minutes. An aliquot of 100 µL of the supernatant mixed with 100 µL of ultra-pure water were used for LC-MS/MS analysis. 7) Solution was discarded from Transwell plates. 100 µL of *Lucifer* Yellow solution (100 µM in HBSS) and 300 µL of HBSS were added into each well of Transwell insert and receiver, respectively, for leakage determination. Plates were incubated at 37° C. for 30 minutes. 80 µL aliquots from wells of apical and basolateral sides were transferred to solid black plates and the plate was read with Tecan Infinite M 200 (Excitation/Emission wavelength 485 nm/530 nm). The liquid fractions, apical and basolateral layers were analyzed by LC-MS to determine $P_{app}$(A-B), $P_{app}$(B-A) and recovery.

Example 17

1 mM ATP Tyk2 Caliper Assay

Compounds were serially diluted in DMSO then further diluted in 1x kinase buffer: 5 uL of buffer diluted compound was added into wells first, then 10 uL of Tyk2 enzyme mix was added into wells, followed by 10 uL of substrate mix to start reaction. Reaction was incubated at 28° C. for 25 min and then added 25 uL stop buffer. The reaction mixture was read by a Caliper mass spectrometer. Final concentrations for assay conditions were: 25 mM HEPES, pH 7.5, 0.01% Brij-35, 0.01% Triton, 0.5 mM EGTA, 2 mM DTT, 10 mM $MgCl_2$, TYK2 4 nM, ATP concentration 1000 uM, and P30 3 uM.

Results of the 1 mM ATP Tyk2 Caliper Assay for various compounds are presented in Table 8.

Example 18

Metabolic Clearance Assay in Microsomes

A master solution was prepared containing 0.5 mg/mL of either rat or human liver microsomes, 5 mM $MgCl_2$, 100 mM phosphate buffer, and 25 ug/mL alamethacin. 40 µL of 10 mM NADPH solution and 40 µL of 20 mM UDPGA solution were added to each well. The final concentrations of NADPH and UDPGA were 1 mM and 2 mM, respectively. The mixture was pre-warmed at 37° C. for 5 minutes. The negative control samples were prepared by replacing NADPH and UDPGA solutions with 80 µL of ultra-pure $H_2O$. The negative control was used to exclude the misleading factor that resulted from instability of chemical itself. This study was performed in duplicate. The reaction was started with the addition of 2 µL of 400 µM control compound or test compound solutions. Diclofenac was used as positive control in this study. The final concentration of test compound or control compound was 2 µM. Aliquots of 50 µL were taken from the reaction solution at 0, 15, 30, 45 and 60 minutes. The reaction was stopped by the addition of 4 volumes of cold acetonitrile (or methanol) with internal standard (IS) (100 nM alprazolam, 200 nM imipramine, 200 nM labetalol and 2 µM ketoprofen) at the designated time points. Samples were centrifuged at 3,220 g for 40 minutes to precipitate protein. Aliquot of 100 µL supernatant diluted by 100 µL of water was used for LC-MS/MS analysis. The in vitro half-life, scale-up intrinsic clearance, and predicted hepatic clearance were calculated according to standard calculations.

Intrinsic clearance values in human liver microsomes (HLM Clint) for selected compounds are presented in Table 8.

Example 19

Kinetic Solubility Determination Assay

Stock solutions of test compounds were prepared in DMSO at the concentration of 10 mM. The stock solutions of positive control compound were prepared in DMSO at the concentration of 30 mM. Progesterone was used as positive control in the assay. 30 µL stock solution of each compound was placed in order into their proper 96-well rack, followed by adding 970 µL of PBS at pH 7.4 into each vial of the cap-less solubility sample plate. This study was performed in duplicate. One stir stick was added to each vial and then vials were sealed using a molded PTDE/SIL 96-Well Plate Cover. The Solubility Sample plate was transferred to the Thermomixer Comfort plate shaker and incubated at RT for 2 hours with shaking at 1100 rpm. After 2 hours incubation, stir sticks were removed using a big magnet and all samples from the Solubility Sample plate were transferred into the filter plate. All the samples were filtered by using the vacuum manifold. The filtered samples were diluted with methanol. Standards of each test compound were prepared at 0.3, 0.09 and 0.1 µM concentrations and both the test samples and standards were analyzed by LC-MS and the test samples were quantified against a standard of known concentration in DMSO using mass spectral peak identification and quantitation.

Results of Kinetic Solubility determinations for selected compounds are presented in Table 8.

Example 21

Dissolution Assay in Fed and Fasted Simulated Gastric and Intestinal Fluids

The dissolution bath was filled with 900 mL of media for testing, the bath temperature held at 37° C., the rotation rate of the apparatus was 50 rpm, the draw point for the sampling probe was set exactly halfway between the surface of the media and the surface of the disc. The test article (0.4 g) was compressed into a disc using a Woods apparatus. The sampling time points were 10, 30, 60, 90, 120, 150 & 180. The samples were analysed by HPLC for concentration against a sample preparation of known concentration (ca. 0.5 mg/ml). Dissolution rate was derived from the curve of concentration against time.

The dissolution rate of Compound 1 in Fasted Simulated Gastric Fluid (FaSSGF) was 57.5 µg/cm$^2$/min, and the dissolution rate of Compound 9 in Fasted Simulated Gastric Fluid was 21.2 µg/cm$^2$/min.

Example 22

Pharmacokinetic Study in Dogs

Male Beagle dogs (9-14 kg; 2.5 to 5.5 years of age) housed one per cage under standard laboratory conditions were fasted for approximately 16 to 17 hours prior to dosing with food returned approximately 2 hours after dosing. Test article was administered by oral gavage at 10 mg/kg formulated in 20% HPβCD aq., pH=5 at 1.0 mg/mL, followed by a 10 mL flush with tap water. Blood samples were collected from the jugular vein (~1.5 mL) by venipuncture, and stored in tubes treated with $K_2$EDTA, then centrifuged (3000 g, 4° C., 5 min). The plasma samples were transferred and stored at −70° C. until analysis. Bioanalysis: Concentrations for experimental samples and plasma calibration standards were determined by LC/MS/MS (API-5500, reverse-phase chromatography, APCI) following extraction by plasma precipitation with cold acetonitrile (4:1 ACN/plasma by volume) containing verapamil as an internal standard. PK Analysis: The individual animal plasma concentration-time data was analyzed by noncompartmental analysis (linear trapazoidal fitting) using PK Solver software (v2.0).

Figure 7:
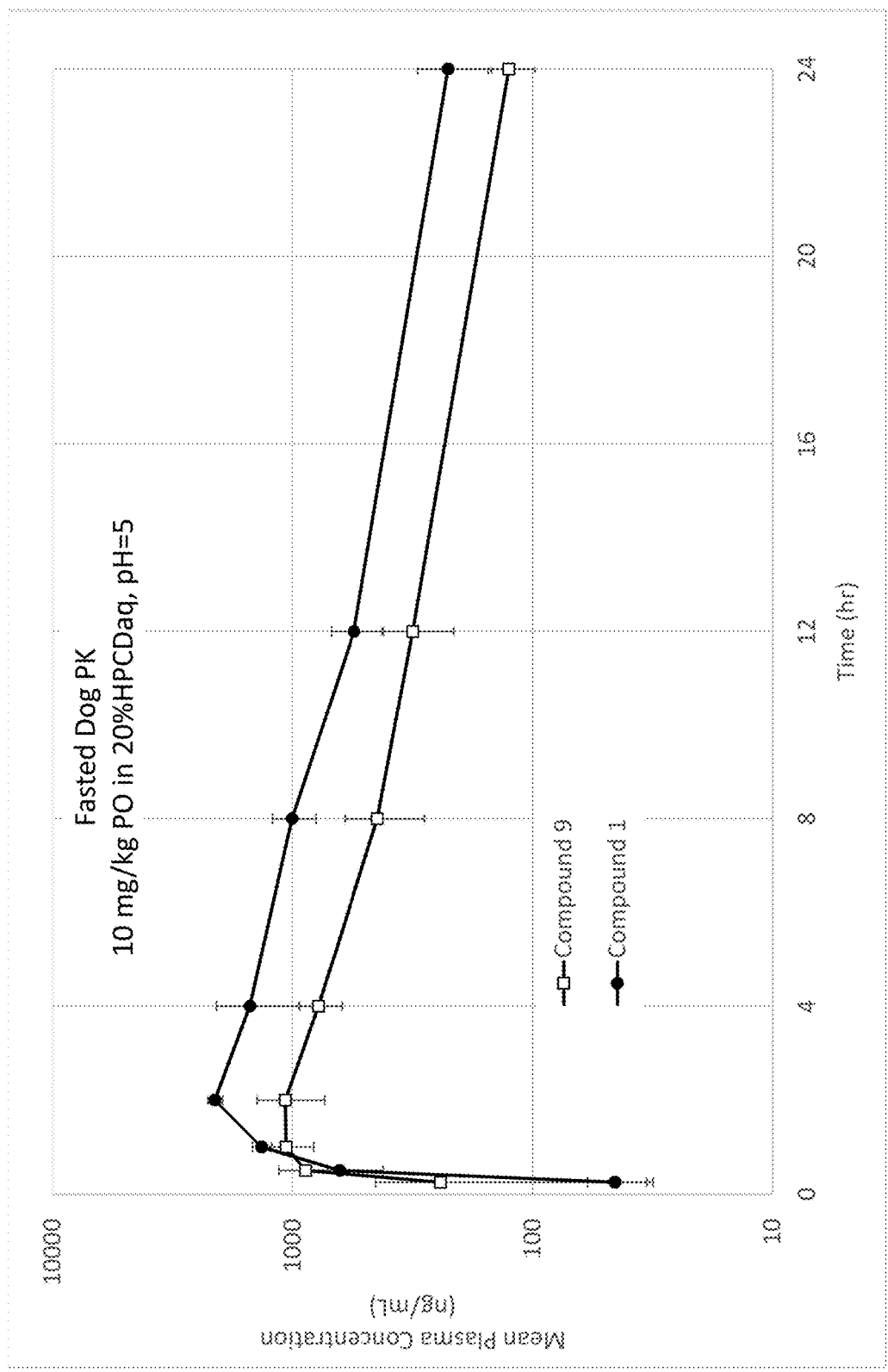
FIG. 7 depicts results of a Pharmacokinetic Study in Dogs for Compound 1 and Compound 9.

Results of a Pharmacokinetic Study in Dogs using Compounds 1 and 9 are depicted in FIG. 7. Compound 1 displayed a Cmax of 2105 ng/mL, while Compound 9 displayed a Cmax of 1071 ng/mL. Compound 1 displayed an AUC (0-t) of 18747 ng*hr/mL and Compound 9 displayed an AUC (0-t) of 10182 ng*hr/mL.

Example 22

Calculation of Topological Polar Surface Area

Polar surface area is calculated according to the method of Ertl et al. J. Med. Chem. (2000), 43, 3714-3717, and values for selected compounds are reported in Table 8.

Example 23

Calculation of Atom-Based Partition Coefficients

A log P values were calculated using the A log P function in Schrodinger LiveDesign 8.1, and values for selected compounds are presented in Table 8.

Structures of various additional compounds useful as compounds useful as Tyk2 inhibitors are depicted in Table 7.

TABLE 7

Structures of Compounds

| Compound Number | Structure |
|---|---|
| 7 | 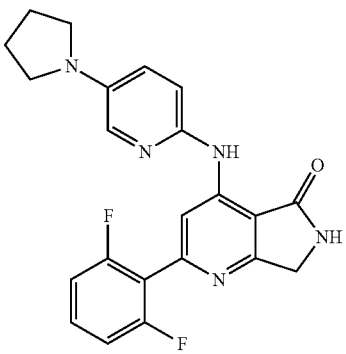 [SMILES: O=C1NCc2nc(-c3c(F)cccc3F)cc(Nc3ccc(N4CCCC4)cn3)c21] |
| 8 | 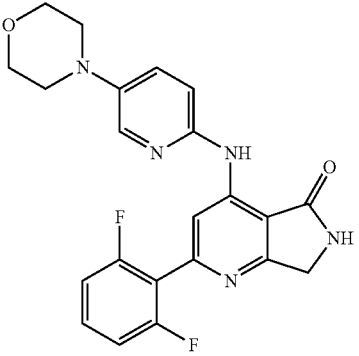 [SMILES: O=C1NCc2nc(-c3c(F)cccc3F)cc(Nc3ccc(N4CCOCC4)cn3)c21] |
| 9 | 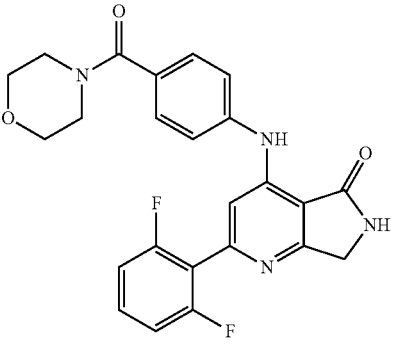 [SMILES: O=C1NCc2nc(-c3c(F)cccc3F)cc(Nc3ccc(C(=O)N4CCOCC4)cc3)c21] |
| 10 | 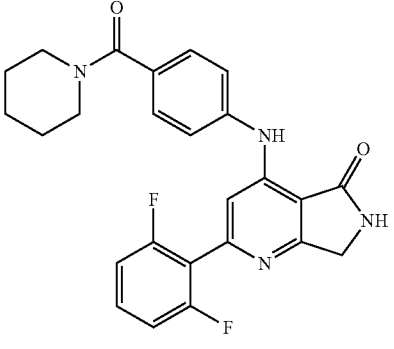 [SMILES: O=C1NCc2nc(-c3c(F)cccc3F)cc(Nc3ccc(C(=O)N4CCCCC4)cc3)c21] |
| 11 | 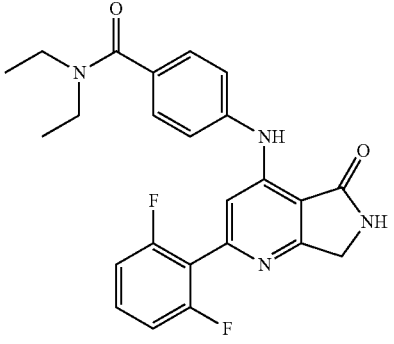 [SMILES: CCN(CC)C(=O)c1ccc(Nc2cc(-c3c(F)cccc3F)nc3c2C(=O)NC3)cc1] |

TABLE 7-continued

Structures of Compounds

| Compound Number | Structure |
|---|---|
| 12 | 4-hydroxy-4-methylpiperidine carbonyl-phenyl-NH-[2-(2,6-difluorophenyl)-5-oxo-6,7-dihydro-5H-pyrrolo[3,4-b]pyridin-4-yl] |
| 13 | morpholine carbonyl-pyridin-2-yl-NH-[2-(2,6-difluorophenyl)-5-oxo-6,7-dihydro-5H-pyrrolo[3,4-b]pyridin-4-yl] |
| 14 | morpholine carbonyl-phenyl-NH-[2-(3-fluoro-2-cyanophenyl)-5-oxo-6,7-dihydro-5H-pyrrolo[3,4-b]pyridin-4-yl] |
| 15 | azetidine carbonyl-phenyl-NH-[2-(2,6-difluorophenyl)-5-oxo-6,7-dihydro-5H-pyrrolo[3,4-b]pyridin-4-yl] |
| 16 | pyrrolidine carbonyl-phenyl-NH-[2-(3-fluoro-2-cyanophenyl)-5-oxo-6,7-dihydro-5H-pyrrolo[3,4-b]pyridin-4-yl] |
| 17 | hexahydrofuro[3,4-c]pyrrole carbonyl-phenyl-NH-[2-(2,6-difluorophenyl)-5-oxo-6,7-dihydro-5H-pyrrolo[3,4-b]pyridin-4-yl] |

TABLE 8

Physicochemical, Pharmacodynamic and Pharmacokinetic Data

| Compound | Tyk2 IC$_{50}$ @ 1 mM ATP (nM) | Kin. Sol. pH 7.4 (μM) | Caco-2 A-B (×10e$^{-6}$ cm/s) | Ertl TPSA (Å$^2$) | AlogP | HLM Clint (mL/min/kg) |
|---|---|---|---|---|---|---|
| 1 | 56.9 | 274.31 | 5.77 | 74.3 | 4.1 | 0.62 |
| 2 | 85.3 | | | 74.3 | 4.1 | |
| 3 | | | | 74.3 | 4.1 | |
| 4 | 78.5 | | | 74.3 | 4.1 | |
| 5 | 72.6 | | | 74.3 | 4.1 | |
| 6 | 93.2 | | | 74.3 | 4.1 | |
| 7 | 390 | <0.5 | 13.47 | 70.2 | 3.9 | 10.91 |
| 8 | 33 | 11.92 | 13.08 | 79.4 | 3.2 | 1.2 |
| 9 | 134 | 171.55 | 3.43 | 83.6 | 3.4 | 3 |
| 10 | 90 | 1.45 | 4.03 | 74.3 | 4.6 | 7.81 |
| 11 | 119 | 1.86 | 5.62 | 74.3 | 4.4 | |
| 12 | 136 | 236.96 | 0.41 | 94.6 | 3.3 | |
| 13 | | 251.64 | 2.89 | 96.5 | 2.6 | 1.9 |

TABLE 8-continued

Physicochemical, Pharmacodynamic and Phamacokinetic Data

| Compound | Tyk2 IC$_{50}$ @ 1 mM ATP (nM) | Kin. Sol. pH 7.4 (μM) | Caco-2 A-B (×10e$^{-6}$ cm/s) | Ertl TPSA (Å$^2$) | AlogP | HLM Clint (mL/min/kg) |
|---|---|---|---|---|---|---|
| 14 | 24.2 | 271.19 | 2.08 | 107.4 | 3.2 | 0 |
| 15 | 74.1 | 3.75 | 7.59 | 74.3 | 3.5 | 1.78 |
| 16 | 17.7 | 32.86 | 2.63 | 98.1 | 4.0 | 0 |
| 17 | 88.6 | 204.67 | 1.52 | 83.6 | 3.1 | |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of Formula I:

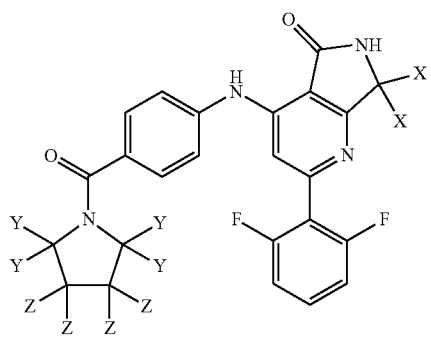

or a pharmaceutically acceptable salt thereof,
wherein each of X, Y, and Z is independently hydrogen or deuterium.

2. The compound of claim 1 of the formula:

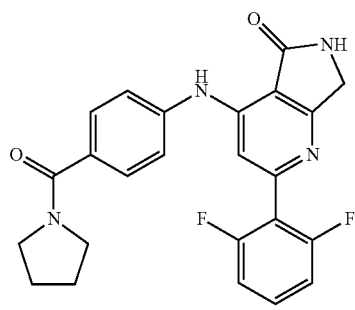 [SMILES: O=C1NCc2nc(-c3c(F)cccc3F)cc(Nc3ccc(C(=O)N4CCCC4)cc3)c21]

or a pharmaceutically acceptable salt thereof.

3. The mesylate salt of the compound of claim 2.
4. The free base of the compound of claim 2.
5. The compound of claim 1, wherein said compound is selected from the group consisting of:

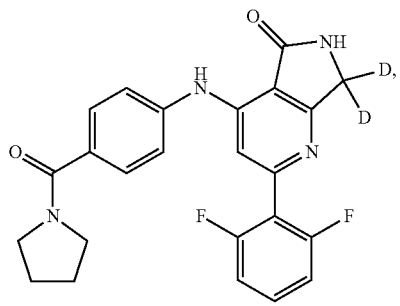

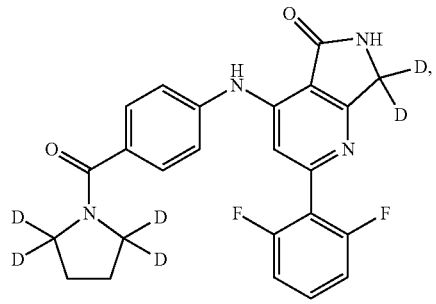

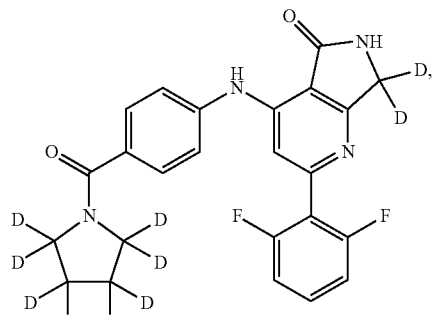

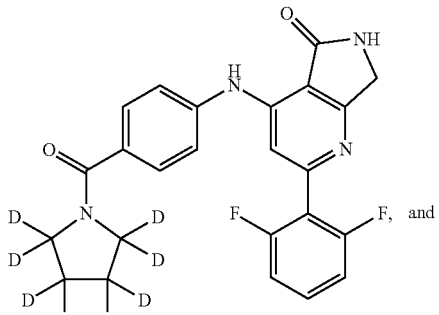

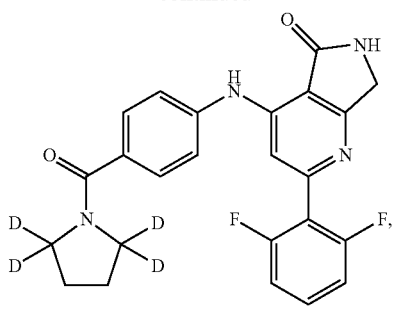

or a pharmaceutically acceptable salt thereof.

6. A solid form of a compound of claim 1.

7. A crystalline form of a compound according to claim 4 having a powder X-ray diffraction (XRPD) pattern as depicted in FIG. 1.

Figure 2:
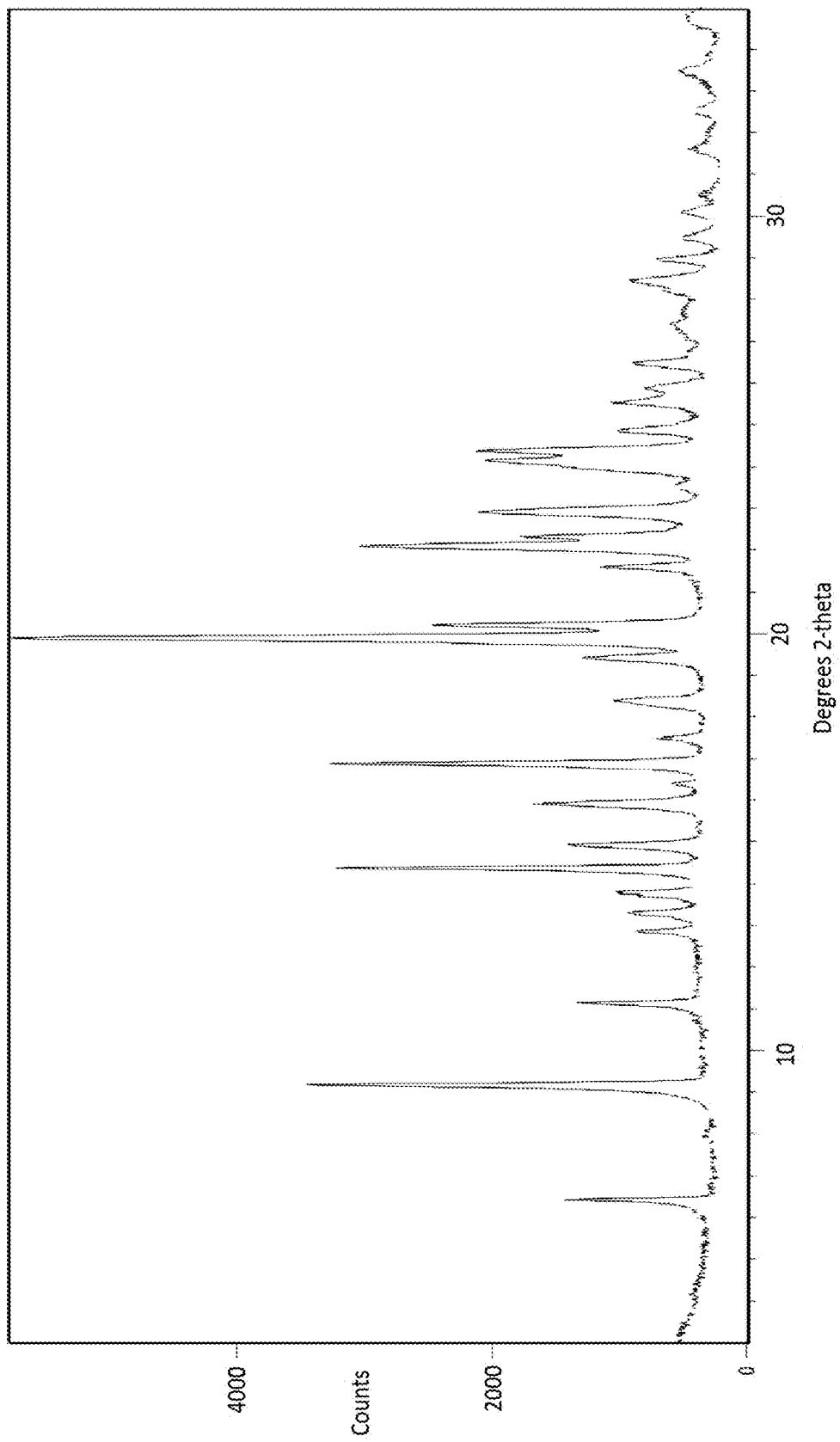
FIG. 2 depicts an X-Ray powder diffraction pattern of Form I of the mesylate salt of Compound 1.

8. A crystalline form of a compound according to claim 3 having a powder X-ray diffraction (XRPD) pattern as depicted in FIG. 2.

Figure 3:
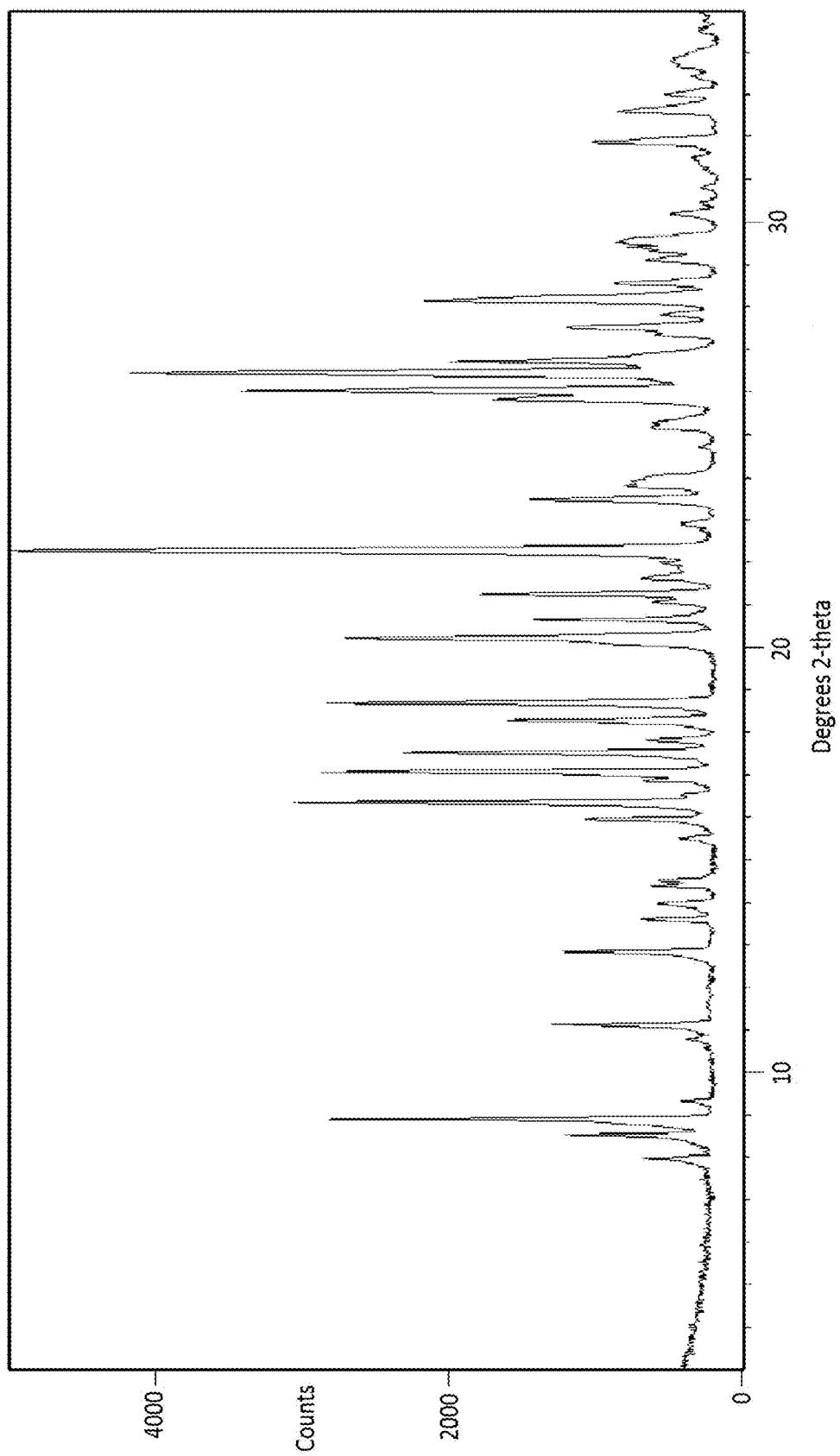
FIG. 3 depicts an X-Ray powder diffraction pattern of Form II of the mesylate salt of Compound 1.

9. A crystalline form of a compound according to claim 3 having a powder X-ray diffraction (XRPD) pattern as depicted in FIG. 3.

Figure 4:
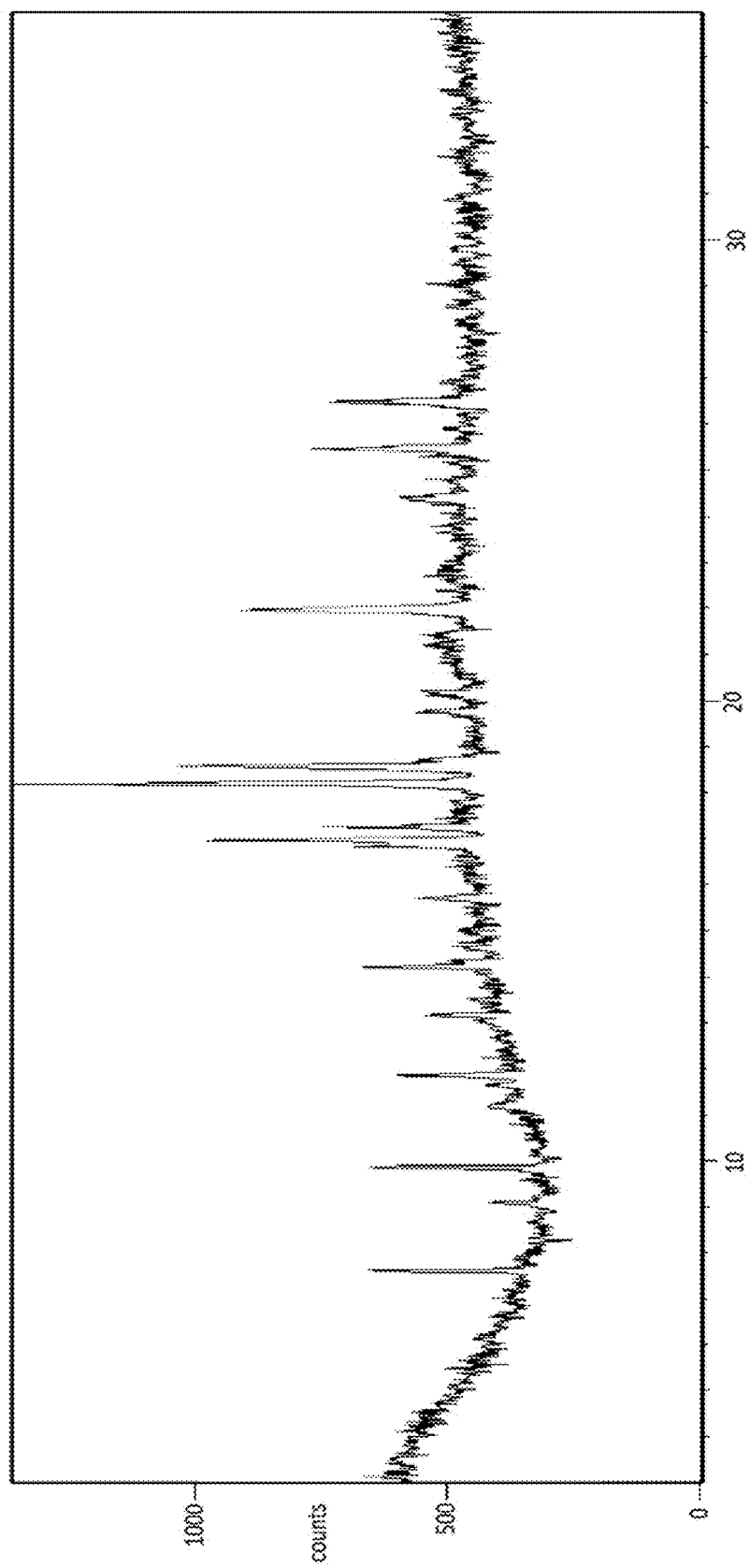
FIG. 4 depicts an X-Ray powder diffraction pattern of Form III of the mesylate salt of Compound 1.

10. A crystalline form of a compound according to claim 3 having a powder X-ray diffraction (XRPD) pattern as depicted in FIG. 4.

Figure 5:
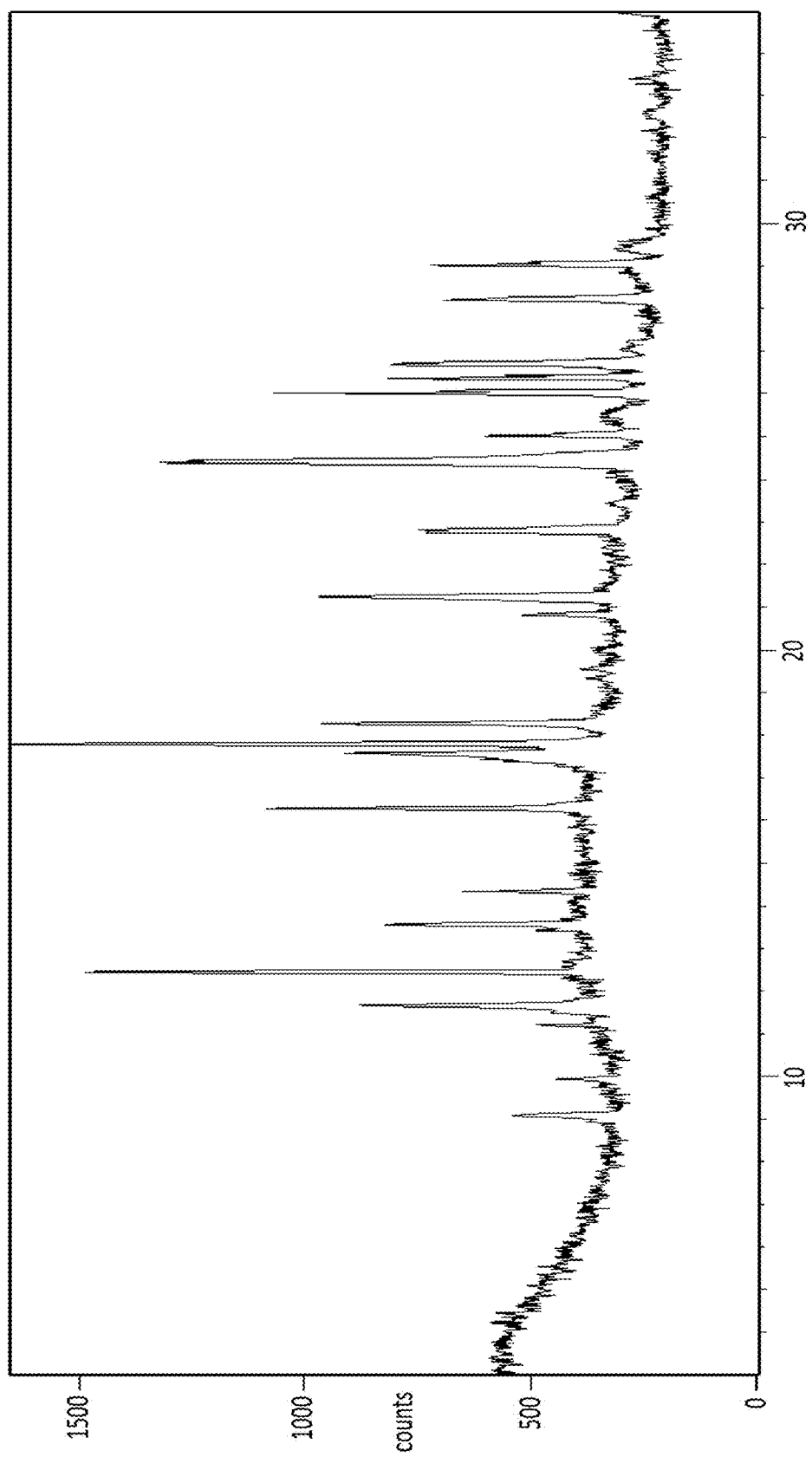
FIG. 5 depicts an X-Ray powder diffraction pattern of Form IV of the mesylate salt of Compound 1.

11. A crystalline form of a compound according to claim 3 having a powder X-ray diffraction (XRPD) pattern as depicted in FIG. 5.

Figure 6:
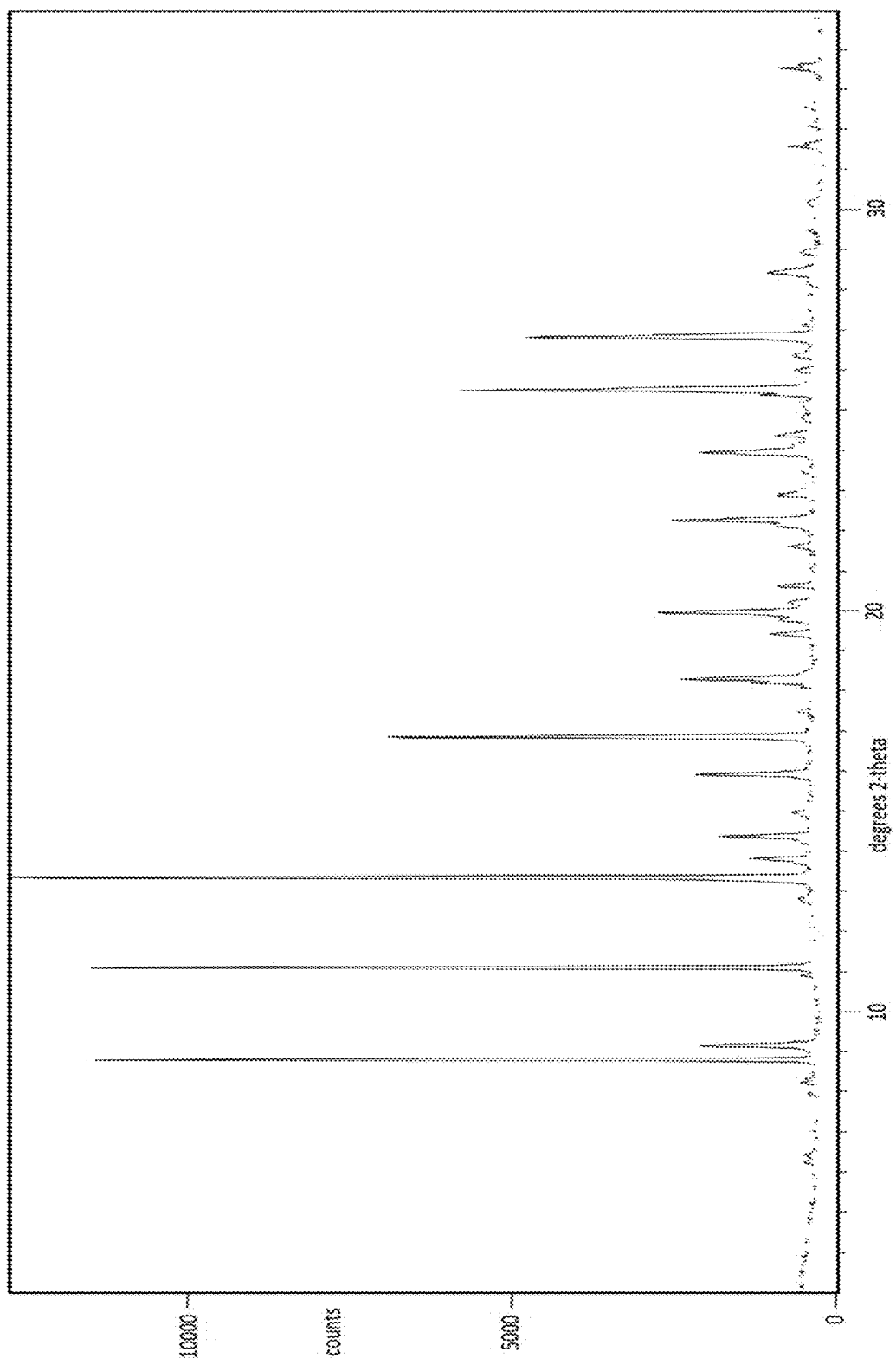
FIG. 6 depicts an X-Ray powder diffraction pattern of Form V of the mesylate salt of Compound 1.

12. A crystalline form of a compound according to claim 3 having a powder X-ray diffraction (XRPD) pattern as depicted in FIG. 6.

13. A process for producing a compound of the formula:

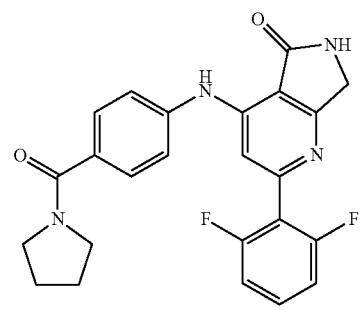 [SMILES: O=C1NCc2nc(-c3c(F)cccc3F)cc(Nc3ccc(C(=O)N4CCCC4)cc3)c21]

comprising contacting a compound of the formula:

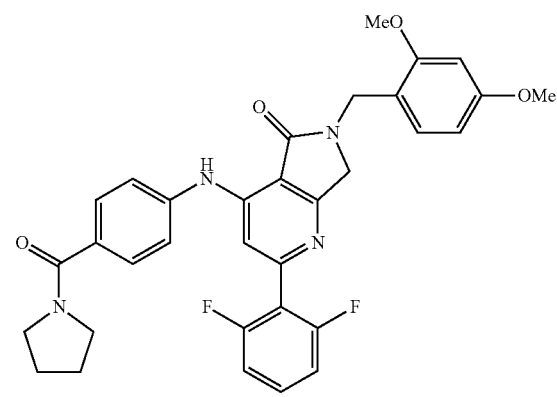 [SMILES: COc1ccc(CN2Cc3nc(-c4c(F)cccc4F)cc(Nc4ccc(C(=O)N5CCCC5)cc4)c3C2=O)c(OC)c1]

with an acid.

14. A process for producing a compound of the formula:

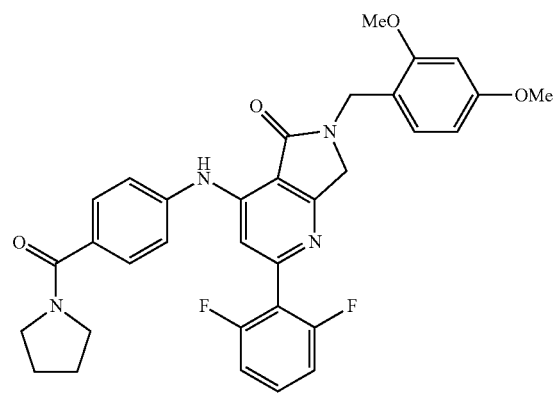 [SMILES: COc1ccc(CN2Cc3nc(-c4c(F)cccc4F)cc(Nc4ccc(C(=O)N5CCCC5)cc4)c3C2=O)c(OC)c1]

comprising contacting a compound of the formula:

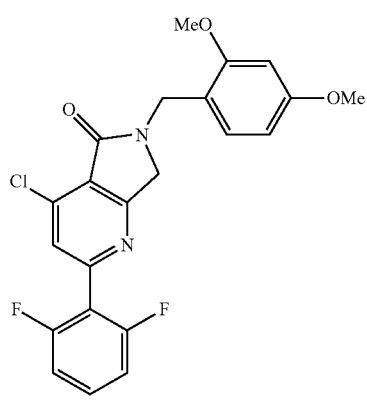 [SMILES: COc1ccc(CN2Cc3nc(-c4c(F)cccc4F)cc(Cl)c3C2=O)c(OC)c1]

with a compound of formula:

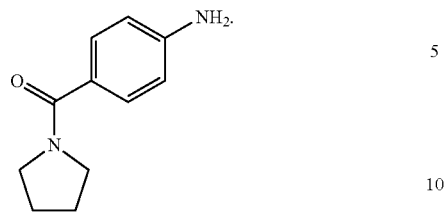

under aryl amination conditions.

15. A pharmaceutical composition comprising a compound according to claim 1 and a pharmaceutically acceptable carrier, adjuvant, or diluent.

16. A method of inhibiting a Tyk2 enzyme in a patient or biological sample comprising contacting said patient or biological sample with a compound according to claim 1.

* * * * *